(12) United States Patent
Sawadogo et al.

(10) Patent No.: US 12,025,601 B2
(45) Date of Patent: Jul. 2, 2024

(54) INTEGRATED MONITORING AND ANALYSIS SYSTEMS AND METHODS

(71) Applicant: FRESHAIR SENSOR LLC, Lebanon, NH (US)

(72) Inventors: Anani Sawadogo, Lebanon, NH (US); Ian DeLaney, Norwich, VT (US); Christopher Billiau, Thetford-Center, VT (US); Manoj Virigineni, Lebanon, NH (US); Kwame Ohene-Adu, Lebanon, NH (US); Taringana Guranungo, Lebanon, NH (US); Matt Curtin, Hanover, NH (US); Katie Shelton, Lebanon, NH (US); Andrei Burnin, West Lebanon, NH (US); Joseph J. BelBruno, Hanover, NH (US)

(73) Assignee: FRESHAIR SENSOR LLC, Lebanon, NH (US)

( * ) Notice: Subject to any disclaimer, the term of this patent is extended or adjusted under 35 U.S.C. 154(b) by 138 days.

(21) Appl. No.: 17/513,791

(22) Filed: Oct. 28, 2021

(65) Prior Publication Data

US 2022/0299492 A1 Sep. 22, 2022

Related U.S. Application Data

(60) Provisional application No. 63/106,532, filed on Oct. 28, 2020.

(51) Int. Cl.
*G01N 33/00* (2006.01)
*G06F 18/2413* (2023.01)
*G08B 21/18* (2006.01)

(52) U.S. Cl.
CPC ....... *G01N 33/0075* (2013.01); *G01N 33/004* (2013.01); *G01N 33/0063* (2013.01); *G06F 18/2414* (2023.01); *G08B 21/182* (2013.01)

(58) Field of Classification Search
CPC ............ G01N 33/0075; G01N 33/004; G01N 33/0063; G01N 33/0036; G01N 33/0067;
(Continued)

(56) References Cited

U.S. PATENT DOCUMENTS 9,429,536 B2 8/2016 BelBruno et al.
10,451,598 B2 10/2019 Belbruno et al.
(Continued)

FOREIGN PATENT DOCUMENTS

KR 20170122043 A * 3/2011 ............. F24F 11/00
WO WO 2013/188675 A1 12/2013
WO WO 2018/028269 A2 2/2019

OTHER PUBLICATIONS

International Patent Application No. PCT/US2021/057133 International Search Report and Written Opinion dated Mar. 18, 2022, 13 pages.

*Primary Examiner* — Benjamin R Schmitt
(74) *Attorney, Agent, or Firm* — Cozen O'Connor

(57) ABSTRACT

Systems and methods monitor a space for environmental pollutants. A sensing device senses and reports air quality anomalies to a cloud detection service. The cloud detection service uses artificial intelligence to analyze raw sensor data from the sensing device, determines whether the raw sensor data indicates an air quality event, and sends an air quality report indicative of the air quality event to a client device associated with the sensing device and/or the monitored space. A sensing device may be deployed in an air extraction vent to detect and report indications of vaping in prohibited spaces. A sensing device may be deployed in a vehicle to detect and report smoking in vehicles where smoking is prohibited. An application running on a mobile device reports detection of a short-range wireless beacon within a (Continued)

serviceable space to a cloud detection service, which tracks servicing of the serviceable space.

15 Claims, 23 Drawing Sheets

(58) Field of Classification Search
CPC .............. F24F 2110/64; F24F 2110/66; F24F 2110/72; F24F 11/58; F24F 11/63; F24F 11/33; G06F 18/2414; G08B 21/182
See application file for complete search history.

(56) References Cited

U.S. PATENT DOCUMENTS

| | | |
|---|---|---|
| 2015/0132857 A1 | 5/2015 | BelBruno et al. |
| 2016/0066068 A1 | 3/2016 | Schultz et al. |
| 2018/0293864 A1* | 10/2018 | Wedig .................... G08B 25/08 |
| 2020/0116686 A1 | 4/2020 | Bertini et al. |
| 2020/0124556 A1 | 4/2020 | BelBruno et al. |

* cited by examiner

1200

Air Quality Status: Moderately Polluted

Property: Lebanon Motels
Room: Room 392 / Main Device
Alert Timestamp: 30 Jun 2020, 11:34 AM Status: Resolved (Duration: 4 hours 35 mins)

Exposure to levels of VOCs* which indicate moderately polluted air quality can cause discomfort, reduction in sleep quality, and health issues including irritation of the eyes, nose, and throat. We recommend inspecting the monitored space and increasing ventilation with clean air.

Notes:
_____

CLOSE    SAVE

* VOCs are volatile organic compounds, as defined in the US Congressional Record 40 CFR Part 51.100(s)

Air Quality Status: Heavily Polluted

Property: Lebanon Motels
Room: Room 392 / Main Device
Alert Timestamp: 30 Jun 2020, 11:34 AM Status: Ongoing Exposure to levels of VOCs which indicate heavily polluted air quality can cause significant health effects including: irritation of the eyes, nose, and throat, headaches, dizziness, and fatigue. We recommend immediately inspecting the monitored space, maximizing ventilation with clean air, and eliminating the source of the contamination as soon as possible.

Notes:
_____

CLOSE    SAVE

* VOCs are volatile organic compounds, as defined in the US Congressional Record 40 CFR Part 51.100(s)

*FIG. 13*

INTEGRATED MONITORING AND ANALYSIS SYSTEMS AND METHODS

RELATED APPLICATION

This application claims priority to U.S. Patent Application No. 63/106,532, titled "Integrated Monitoring and Analysis Systems and Methods," filed Oct. 28, 2020, and incorporated herein in its entirety by reference.

FIELD OF INVENTION

This invention is related to the use of sensors and machine learning software for monitoring the ambient atmosphere for the presence of a chemical that may cause harm to those living or working in the monitored space. The output of a PolySens® sensor is analyzed to determine a vaping target in conjunction with temperature, relative humidity, and volatile organic-compound detection.

BACKGROUND

Smoking (of tobacco, marijuana, and vaping) is prohibited in many spaces. The odor left by tobacco smoke, for example, is instantly recognizable and disliked by non-smoking members of the population. However, smoking still occurs in prohibited spaces, and causes inconvenience to owners needing additional time to clean the space and to subsequent users of the space, since smoke residue and odor is difficult to remove.

Servicing rooms in a hotel is complicated, since guests arrive and depart at varying times. Servicing personnel use paper lists that are marked to track servicing requirements, but easily lose track of which rooms have been serviced and which are awaiting service.

SUMMARY

In an embodiment, the integrated monitoring and analysis system disclosed herein uses a distributed computing paradigm, e.g., a combination of edge and cloud processing, to provide a real time, scalable, configurable, and accurate detection of sensed air (e.g., smoking) events in a monitored space. At least one sensing device deployed in the monitored space implements edge processing, and communicates with a cloud detection service. The sensing device senses air quality at the monitored space, collects data, detects anomalies in the data, and reports the detected anomalies to the cloud detection service. When an anomaly is reported, the cloud detection service retrieves collected data from the sensing device and runs a more elaborate evaluation of the data to determine whether an air quality event has occurred. When an air quality event occurs, the cloud detection service dispatches an alert to an appropriate endpoint based on the results of the evaluation. The sensing device includes multiple sensors, some for detecting ambient conditions, and others that are molecularly specific and sense presence of specific environmental toxins or other chemicals in the air that create an unsafe or unwanted atmosphere in the monitored space. The cloud detection service may use a machine learning algorithm to discern whether the data received from the sensing device indicates the air quality event at the monitored space.

Electronic cigarette use has rapidly expanded to groups other than cigarette smokers attempting to quit smoking. Vaping devices, used to inhale both marijuana vapor and nicotine vapor are used by populations likely never to have taken up smoking. Compact devices are in widespread use among teenagers creating addiction in groups that are not conventional smokers. In addition, studies have shown that propylene glycol, the primary vapor constituent since it is used to solubilize the active component, may form the carcinogenic propylene oxide molecule. The use of compact vaping devices is easily concealed. The devices are the size of a thumb drive and their use leaves no lingering cigarette smoke or cigarette breath. The use of a sensor for detecting vaping can be a valuable tool in stopping and preventing the use of vaping and limiting the harmful effects thereof. The real-time system described herein would aid in that realization.

Smoking (marijuana and tobacco) in vehicles is often prohibited, since the odor of stale smoke is undesirable and is difficult to remove, since the smoke leaves a residue and the undesirable odor on the various surfaces in a vehicle. The odor is instantly recognizable, especially by most of the population that is non-smoking. Removing the residue and odor is a laborious, time-consuming process that includes treating all surfaces, requiring that the vehicle is removed from service typically for at least one day. Accordingly, when a rental vehicle is returned and smoking has occurred, that vehicle is unsuitable for subsequent rentals until thoroughly cleaned. Often, the cleaning process cannot remove the residue and odor sufficiently, rendering the vehicle unsuitable for further rental, and the rental agency may therefore offer it for sale. However, the presence of the lingering odor also reduces the resale value of the vehicle, and may make the vehicle unsalable. The present embodiments provide a sensor for a vehicle that detects, logs, and reports marijuana and tobacco smoke.

A guest's valuation of a hotel is often based on their impression when first entering their allocated room. Accordingly, it is important that the hotel maintain high quality standards when preparing their rooms for guests, particularly for newly arrived guests. However, the complexity of scheduling hotel room servicing is complicated by guests departing the hotel at different times, requiring the servicing personnel to track which rooms have been completed and which require further attention. Similarly, when a guest requests room service, it is important to fulfil that request timely. The present embodiments provide a beacon device in each serviceable space and an application that runs on a mobile device carried by service personnel. The application detects a short-range wireless beacon generated by the beacon device when the service personnel enter the serviceable room, and reports the detected beacon to a cloud detection service. The detection service uses the detected beacon the determine when the servicing personnel visit the serviceable space and provides an interface that allows a supervisor to define and track servicing requirements and improve servicing quality.

In one embodiment, a method generates an air quality event alert for a monitored space having a sensing device. A cloud detection service receives, from the sensing device, an anomaly detected report including a timestamp for an air quality anomaly detected at the monitored space. Raw sensor data captured by the sensing device using a plurality of sensors during a period including the timestamp is retrieved and characteristics and metrics are extracted from the raw sensor data for each of the plurality of sensors. The characteristics and metrics are processed through a model prediction service to generate probabilities indicative of the characteristics and metrics corresponding to profiles of air quality events, and the probabilities are assembled to generate a score for the air quality anomaly corresponding to an important air quality event. An air quality report is sent when the score is higher than a first threshold corresponding to significant air quality events.

In another embodiment, a method detects an air quality anomaly at a monitored space. The method includes: capturing, at intervals in a sensing device located at the monitored space, raw sensor data from at least one environmental sensor, at least one carbon monoxide (CO) sensor, and at least one polymer sensor; processing, using a smoothing algorithm, the raw sensor data to generate smoothed sensor data; calculating, for at least the CO sensor and the at least one polymer sensor, a difference between the smoothed sensor data and a baseline; driving, for at least the CO sensor and the at least one polymer sensor, a state machine to change state between a clean air state, an anomalous behavior state, and an anomaly detected state, based upon the difference; and sending an anomaly detected report, indicating the air quality anomaly, to a cloud detection service when the state is the anomaly detected state.

In another embodiment, a system monitors air quality of a monitored space. The system includes: at least one sensing device, located at the monitored space, the at least one sensing device having: at least one environmental sensor positioned to sense a characteristic of air within the monitored space; at least one carbon monoxide (CO) sensor positioned to sense a level of CO in the air; at least one polymer sensor positioned to sense a level of a targeted molecule in the air; an interface for communicating with a local network; a processor communicatively coupled with a memory; and detector firmware stored in the memory and having machine-readable instructions that, when executed by the processor, control the processor to: capture, at intervals, raw sensor data from the at least one environmental sensor, the at least one CO sensor, and the at least one polymer sensor; process, using a smoothing algorithm, the raw sensor data to generate smoothed sensor data; calculate, for at least the CO sensor and the at least one polymer sensor, a difference between the smoothed sensor data and a baseline; drive, for at least the CO sensor and the at least one polymer sensor, a state machine to change state between a clean air state, an anomalous behavior state, and an anomaly detected state, based upon the difference; and send, via the interface, an anomaly detected report, indicating an air quality anomaly, to a cloud detection service when the state is the anomaly detected state. The cloud detection service including: a collection service for receiving the anomaly detected report and for receiving the raw sensor data from the at least one sensing device; a model prediction service for processing characteristics and metrics of the raw sensor data to generate probabilities indicative of the characteristics and metrics corresponding to profiles of air quality events; a prediction assembling service for assembling the probabilities to generate a score for the air quality anomaly; and sending an air quality report when the score is higher than a first threshold, the first threshold defining a value corresponding to a high probability that the raw sensor data indicates a significant air quality event.

In another embodiment, a computer-readable media stores machine-readable instructions that, when executed by a computer, perform steps for detecting an air quality anomaly at a monitored space, including: instructions for capturing, at intervals, raw sensor data from at least one environmental sensor, at least one carbon monoxide (CO) sensor, and at least one polymer sensor; instructions for processing, using a smoothing algorithm, the raw sensor data to generate smoothed sensor data; instructions for calculating, for at least the CO sensor and the at least one polymer sensor, a difference between the smoothed sensor data and a baseline; instructions for driving, for at least the CO sensor and the at least one polymer sensor, a state machine to change state between a clean air state, an anomalous behavior state, and an anomaly detected state, based upon the difference; and instructions for sending an anomaly detected report, indicating the air quality anomaly, to a cloud detection service when the state is the anomaly detected state.

In another embodiment, a method automatically detects when a sensor requires replacement, the method including: receiving, within a cloud detection service and from a sensing device, raw sensor data from the sensor; processing, using a long-term exponential smoothing algorithm, the raw sensor data to generate baseline values; determining that the sensor has failed when the baseline values are not within an operational baseline range of the sensor; and notifying a customer support team of the failed sensor.

In another embodiment, a method detects vaping in a space where vaping is prohibited, including: capturing, at intervals by a sensor module positioned within an air extraction duction of the space, raw sensor data from at least one polymer sensor; processing, using a smoothing algorithm, the raw sensor data to generate smoothed sensor data; calculating, for the at least one polymer sensor, a difference between the smoothed sensor data and a baseline; sending, via the interface, an alert and raw sensor data to a control module when the difference is greater than a threshold; processing, within the control module, the raw sensor data to detect the vaping; and sending a vaping report indicative of the detected vaping.

In another embodiment, a system detects vaping in a space where vaping is prohibited, the system including: a sensor module having: a housing sized and shaped to fit within an air extraction duct fluidly coupled with the space; at least one polymer sensor positioned within the housing to receive air flowing through the air extraction duct and operable to sense a level of a targeted molecule associated with vaping; a first short range wireless interface; a processor communicatively coupled with a memory; and detector firmware stored in the memory and having machine-readable instructions that, when executed by the processor, control the processor to: capture, at intervals, raw sensor data from the at least one polymer sensor; and send, via the first short range wireless interface, a first message including raw sensor data to a control module. The control module having: a second short range wireless interface; a network interface; a second processor communicatively coupled with a second memory; and controller firmware stored in the second memory and having machine-readable instructions that, when executed by the processor, cause the second processor to: receive the first message via the second short range wireless interface; process, using a smoothing algorithm, the raw sensor data to generate smoothed sensor data; calculate, for the at least one polymer sensor, a difference between the smoothed sensor data and a second baseline; drive, based upon the difference for the at least one polymer sensor, a state machine to change state between a clean air state, an anomalous behavior state, and an anomaly detected state; and send an anomaly detected report, indicating vaping is detected when the state is the anomaly detected state.

In another embodiment, a method detects smoking in a vehicle where smoking is prohibited, including: capturing, at intervals by a sensing device positioned within the vehicle, raw sensor data from at least one polymer sensor; processing, using a smoothing algorithm, the raw sensor data to generate smoothed sensor data; calculating, for the at least one polymer sensor, a difference between the smoothed sensor data and a baseline; driving, for the at least one polymer sensor, a state machine to change state between a clean air state, an anomalous behavior state, and an anomaly detected state, based upon the difference; and sending, via a wireless interface of the sensing device, an anomaly detected report indicating the detected smoking.

In another embodiment, a system detects the occurrence of smoking in a vehicle where smoking is prohibited, including: a sensor module having: a housing sized and shaped to fit within a cabin of the vehicle; at least one polymer sensor positioned within the housing and operable to sense a level of a targeted molecule associated with smoking in air within the cabin; a wireless interface; a processor communicatively coupled with a memory; and detector firmware stored in the memory and having machine-readable instructions that, when executed by the processor, control the processor to: capture, at intervals, raw sensor data from the at least one polymer sensor; processing, using a smoothing algorithm, the raw sensor data to generate smoothed sensor data; calculating, for the at least one polymer sensor, a difference between the smoothed sensor data and a baseline; driving, for the at least one polymer sensor, a state machine to change state between a clean air state, an anomalous behavior state, and an anomaly detected state, based upon the difference; and sending, via the wireless interface, an anomaly detected report indicating detected smoking to a cloud detection service when the state is the anomaly detected state.

In another embodiment, a service quality control method includes: generating a beacon using a wireless interface of a beacon device positioned within a serviceable space; receiving, from a mobile device in response to the mobile device detecting the wireless beacon, a first message including a mobile device identifier (ID) that uniquely identifies the mobile device and a beacon ID, decoded from the beacon, that uniquely identifies the beacon device; and updating a database to indicate the association of the mobile device ID with the beacon ID to indicate servicing of the serviceable space.

BRIEF DESCRIPTION OF THE FIGURES

FIG. 12 shows one example mildly-polluted alert presented to the user on the client device, in embodiments.

FIG. 13 shows one example heavily-polluted alert presented to the user on the client device, in embodiments.

DETAILED DESCRIPTION OF THE EMBODIMENTS

Figure 1:
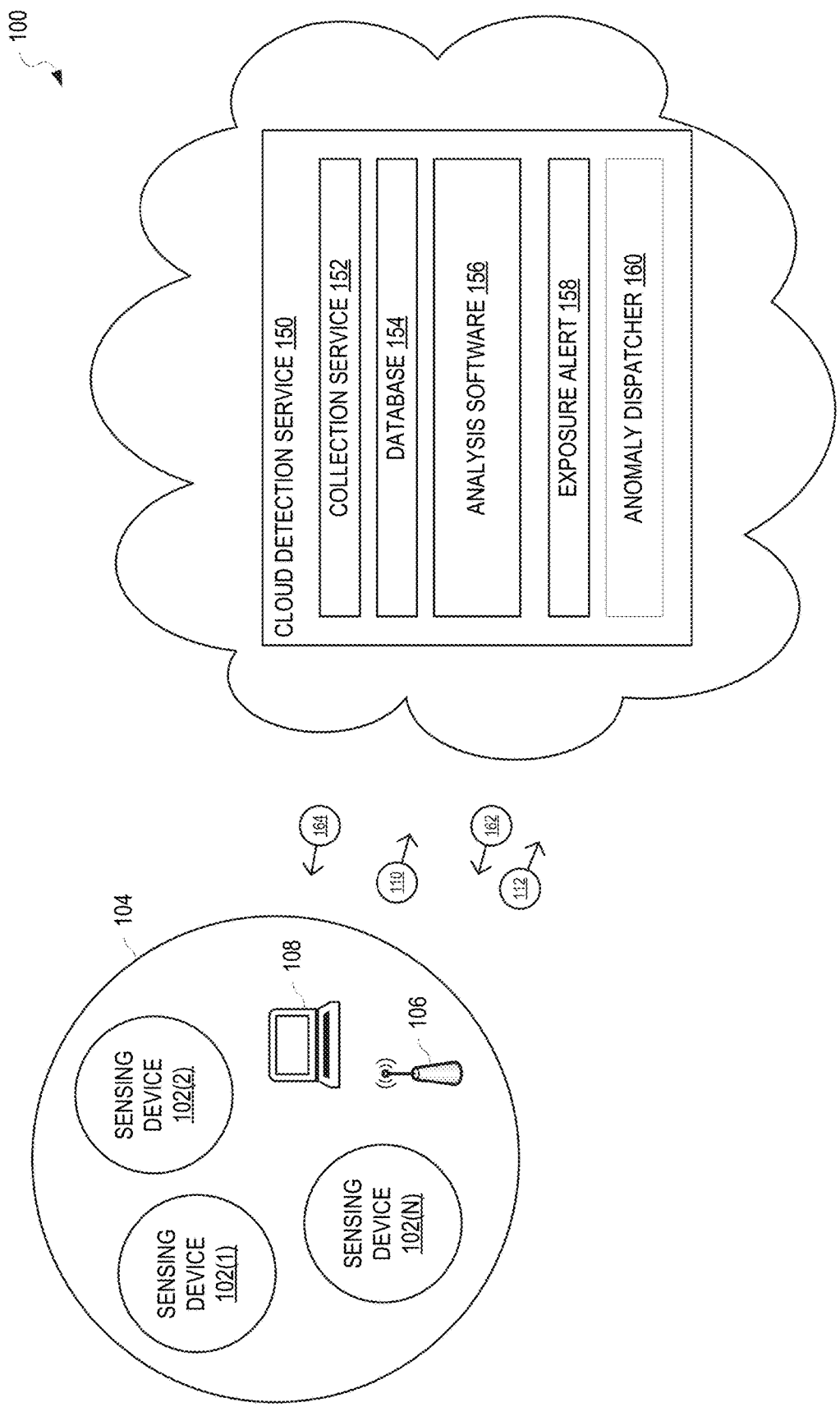
FIG. 1 shows one integrated monitoring and analysis system, in embodiments.

FIG. 1 shows one integrated monitoring and analysis system 100, used for example to check air quality in monitored spaces 104. System 100 includes at least one sensing device 102 deployed to monitor air quality at a monitored space 104 and a cloud detection service 150. In one example of use, monitored space 104 represents a hotel and sensing devices 102(1)-(N) are each deployed in different guest rooms of the hotel to monitor air quality. System 100 is highly scalable and more or fewer sensing devices 102 may be deployed at many different monitored spaces 104 without departing from the scope hereof.

Sensing devices 102 may communicate with a collection service 152 (e.g., a communication interface) of cloud detection service 150 via a local network 106 using one or more wireless (or wired) protocols, including Wi-Fi, Bluetooth, Zwave, ZigBee, and so on. Local wireless network 106 may connect to the Internet for example. A database 154 of cloud detection service 150 may associate a client device 108 (e.g., a computer, laptop, tablet, smartphone, etc.) with monitored space 104 and/or sensing device 102. For example, where sensing device 102 is deployed in a guest room of a hotel, client device 108 may be used by a manager of the hotel. When sensing device 102 detects an anomaly in air quality of monitored space 104, sensing device 102 sends a message 110 identifying itself and indicating a time of the anomaly to cloud detection service 150.

In certain embodiments, each sensing device 102 buffers raw sensor data and waits for collection service 152 to request raw data corresponding to message 110 reporting the time of the anomaly. For example, collection service 152 sends a message 162 requesting sensor data from the identified sensing device 102, which, in response, sends the corresponding sensor data, shown as message 112, to cloud detection service 150. In other embodiments, collection service 152 may receive raw sensor data from each sensing device 102 at intervals (e.g., as blocks of data), or continuously as it is captured. Accordingly, when sensing device 102 sends message 110 identifying itself and indicating the time of the anomaly to cloud detection service 150, raw sensor data corresponding to the anomaly has already been received by collection service 152.

Analysis software 156 of cloud detection service 150 further analyzes the raw sensor data and generates an exposure alert 158 based on a determined cause of the air quality anomaly. As described in detail below, analysis software 156 may use artificial intelligence (AI) algorithms and techniques to analyze raw sensor data captured from at least two different sensors of sensing device 102 to determine a cause of exposure alert 158. Analysis software 156 may implement self-learning to improve analysis and detection of air quality anomalies over time. An anomaly dispatcher 160 of the cloud detection service 150 identifies client device 108 as being associated with monitored space 104 and sends a message 164 including exposure alert 158 to client device 108.

Figure 2:
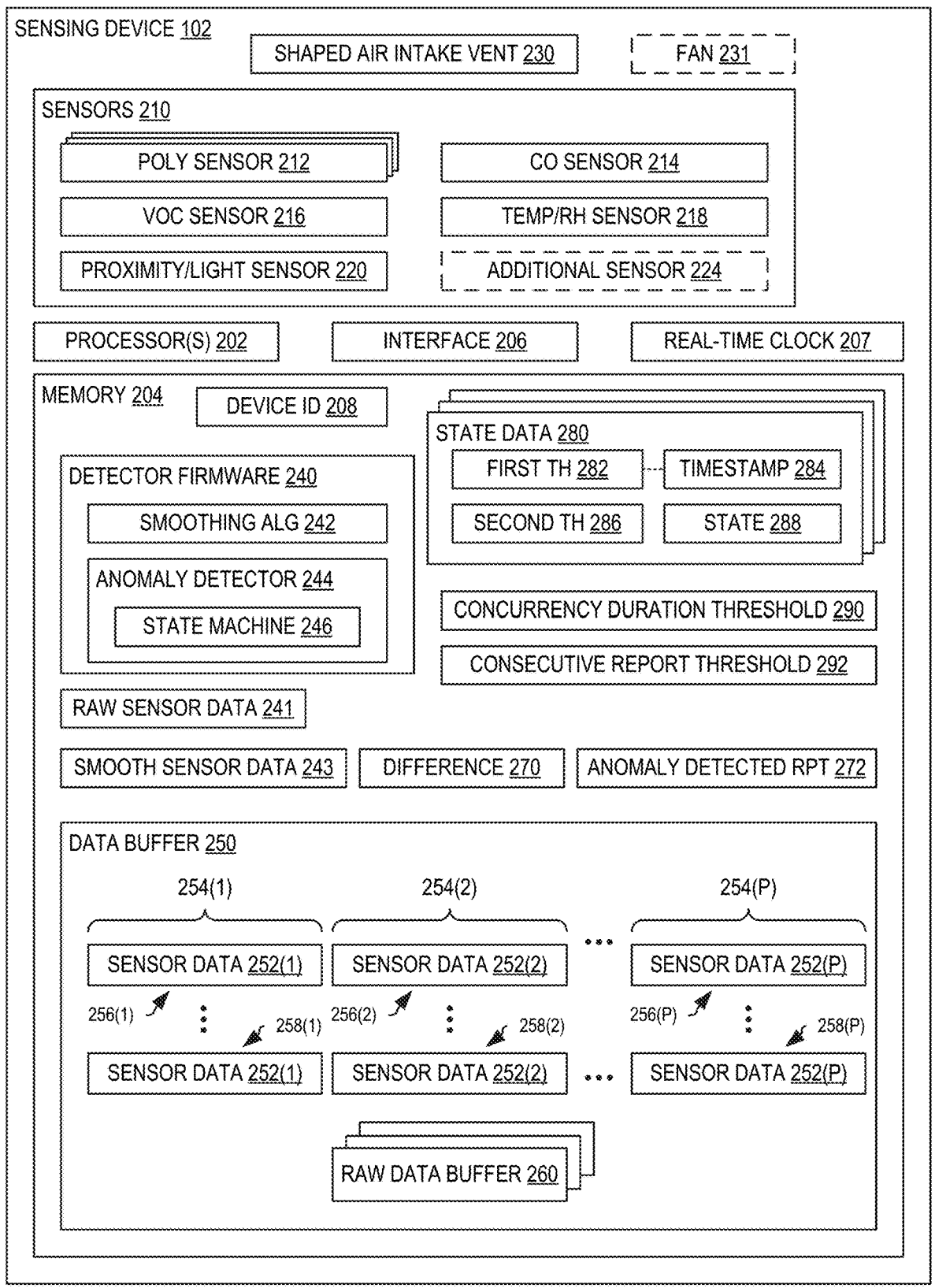
FIG. 2 shows the sensing device of FIG. 1 in further example detail, in embodiments.

FIG. 2 shows sensing device 102 of FIG. 1 in further example detail. FIGS. 1 and 2 are best viewed together with the following description. Sensing device 102 may include a plurality of sensors 210, including at least one polymer sensor 212 that senses a level of a targeted molecule in the air, and a carbon monoxide (CO) sensor 214 that senses a level of CO in the air, and one or more environmental sensors such as a volatile organic compound (VOC) sensor 216, a temperature/relative humidity/atmospheric pressure sensor 218, and a proximity/light sensor 220. In certain embodiments, sensing device 102 is configurable to include up to three different types of polymer sensors 212, each detecting a different environmental pollutant in the ambient air such as one or more of tobacco smoke, marijuana smoke, toxic industrial chemicals, bacteria, etc. The environmental sensors may sense temperature, relative and/or absolute humidity, volatile organic chemical concentration, atmospheric pressure, and so on, and may be used to calibrate the response of the molecule specific sensors 212, 214. Sensing device 102 may include one or more additional sensors 224 without departing from the scope hereof. Sensors 210 are positioned, within a housing of sensing device 102, to experience an airflow via a shaped air intake vent 230. In certain embodiments, the airflow may be aided by a fan 231.

Sensing device 102 may include at least one processor 202 communicatively coupled with memory 204 storing detector firmware 240 that includes machine-readable instructions which, when executed by processor 202, cause processor 202 to implement functionality of sensing device 102 as described herein. Sensing device 102 may also include an interface 206 for communicating with at least local wireless network 106 and a real-time clock 207 that maintains a current time and date. In certain embodiments, interface 206 (and/or detector firmware 240) may implement a Bluetooth beacon, described in further detail below. In certain embodiments, detector firmware 240 and interface 206 may implement a Message Queuing Telemetry Transport (MQTT) protocol, operating over the TCP/IP network, to communicate with cloud detection service 150. The MQTT protocol enables two-way communication such that cloud detection service 150 may initiate communication to individual sensing devices 102 when needed (e.g., to send sensing parameter updates, Wi-Fi network updates, and so on), to prevent data loss by implementing the different levels of packet reception acknowledgment (e.g., quality of service), and to reduce the size of transmitted data as compared to the regular HTTP protocol. Detector firmware 240 may synchronize, once and/or periodically, real-time clock 207 to an online time service as known in the art. In other embodiments, detector firmware 240 may implement and maintain real-time clock 207 in memory 204 using software. Sensing device 102 may also implement the HTTP protocol to send and/or receive one or more of status, operation logs, updated parameters, and firmware, with cloud detection service 150, particularly when the MQTT protocol is disabled or blocked by a client Wi-Fi network (e.g., based on firewall settings).

Memory 204 also stores a device ID 208 that uniquely identifies sensing device 102 to cloud detection service 150. For example, device ID 208 may be included within messages sent by sensing device 102 to cloud detection service 150 such that cloud detection service 150 attributes the messages and their content to the correct sensing device 102.

Memory 204 also includes a data buffer 250 for storing sensor data 252 determined from at least one of sensors 210. In certain embodiments, data buffer 250 may implement, for each sensor 210, an independent cyclic buffer 254 that stores several minutes' worth of sensor data 252. In one embodiment, data buffer 250 stores sensor data 252 for a period of five-minutes (e.g., three hundred sensor data 252 entries for each sensor when sensor data 252 is determined at a rate of one per second). However, in certain other embodiments, data buffer 250 may be larger and store more than five-minutes' worth of sensor data 252. In the example of FIG. 2, data buffer 250 is shown with P (an integer greater than or equal to 3) cyclic buffers 254(1)-(P), each storing sensor data for a different one of sensors 210 and each having a head 256(1)-(P) and a tail 258(1)-(P). Data buffer 250 may also store, for each of sensors 210, a raw data buffer 260 that stores raw sensor data read from each of sensors 210. Each raw data buffer 260 is implemented as a cyclic buffer that stores at least forty-five-minutes' worth of raw sensor data 241 read from one of sensors 210. Accordingly, sensing device 102 also maintains a history of raw sensor data captured over the last forty-five minutes.

Detector firmware 240 includes a smoothing algorithm 242 and an anomaly detector 244. Detector firmware 240 reads raw sensor data (shown as raw sensor data 241 in memory 204) from at least one of sensors 210 at intervals (e.g., once per second), stores the raw sensor data 241 in the corresponding raw data buffer 260, invokes smoothing algorithm 242 to process the raw data and determine smoothed sensor data 243, and stores smoothed sensor data 243 at head 256 of the corresponding cyclic buffer 254 of data buffer 250, where it is shown as sensor data 252. For example, detector firmware 240 may use an internal timer of processor 202 to determine an interval of one second between reading of raw sensor data from polymer sensor 212. In certain embodiments, smoothing algorithm 242 is an exponential smoothing function that is parametrized to dampen fast deviations in raw data read from sensors 210. Data buffer 250 thereby maintains, in combination with smoothing algorithm 242, a baseline for each monitored sensor that may change (e.g., drift slowly) over time. An anomaly in air quality is identified when sensed conditions change faster than expected. That is, sensed conditions of clean air are expected to change gradually (e.g., change by small amounts over long periods). Accordingly, the corresponding baseline may also change gradual over time. For example, each cyclic buffer 254 stores the smoothed sensor data 243 for at least five minutes, where sensor data 252 at tail 258 of cyclic buffer 254 is smoothed sensor data 243 that was calculated five minutes ago. Cyclic buffers 254 may be configured to store sensor data 252 for other periods without departing from the scope hereof. In certain embodiments, the period of cyclic buffers 254 is configurable by cloud detection service 150.

To detect anomalies in the air quality, detector firmware 240 invokes anomaly detector 244 to evaluate smoothed sensor data 243 for one or more of sensors 210 against a corresponding baseline for that sensor. Using the example of FIG. 2, where sensing device 102 includes polymer sensor 212 and CO sensor 214, anomaly detector 244 may be configured to monitor sensor data 252 for only these sensors. For each monitored sensor, anomaly detector 244 compares the most recently determined sensor data 252 (e.g., after the raw data is processed by smoothing algorithm 242) with a baseline value read from tail 258 of the corresponding cyclic buffer 254 of data buffer 250 for that sensor to determine a difference 270. For example, where cyclic buffer 254(1) stores sensor data 252(1) corresponding to polymer sensor 212, anomaly detector 244 may determine difference 270 by subtracting sensor data 252(1) at tail 258(1) of cyclic buffer 254(1) and sensor data 252(1) at head 256(1) of cyclic buffer 254(1). That is, difference 270 represents change from a smoothed sensed value that occurred five minutes ago and a current smoothed sensed value. Accordingly, difference 270 represents changes in sensed air quality that has occurred within the last five-minute period.

Certain aspects of the present embodiments include the realization that false positive may occur when a simple threshold value is used to trigger air quality anomalies, since one or more sample values greater than a trigger threshold may occasionally occur without a significant air quality anomaly. Advantageously, the present embodiments solve this problem by including a state machine 246 in anomaly detector 244 that detects when a slope of consecutive differences in sensor data 252 for each monitored sensor indicates a continued change (increase or decrease) in sensor data 252 and thereby more strongly indicates when to send an anomaly report to cloud detection service 150 as compared to evaluating a single difference. Particularly, state machine 246 confirms when a change indicated by a monitored sensor is consistent. Advantageously, state machine 246 reduces the number of air quality anomaly false positives indicated by sensing device 102.

Figure 3:
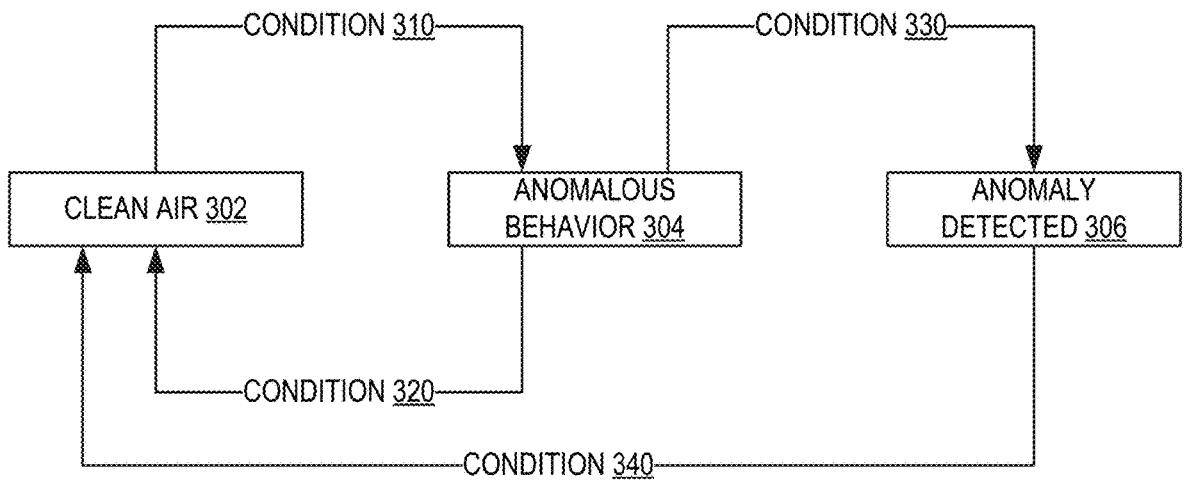
FIG. 3 shows the state machine of FIG. 2 in further example detail, in embodiments.

FIG. 3 is a block diagram illustrating example detail of state machine 246 of FIG. 2. State machine 246 is invoked by anomaly detector 244 to independently monitor at least two different ones of sensors 210, maintaining, for each monitored sensor, state data 280 that includes a first threshold 282 corresponding to the determined difference in sensor data 252, a timestamp 284 for storing when the anomaly was detected, a second threshold 286 corresponding to a second determined difference (e.g., the slope) in sensor data 252, and a current state 288 of state machine 246 for the sensor. Second threshold 286 may be the same as first threshold 282, or may be different. First threshold 282 and second threshold 286 define a slope that sensor data 252 is required to indicate for the anomaly in air quality to be reported. First and second thresholds 282 and 286 may be selected to eliminate the risk of false negatives while minimizing the number of false positives being reported by sensing device 102. Continuing with the example of FIG. 2, where sensing device 102 includes polymer sensor 212 and CO sensor 214, memory 204 may store two instances of state data 280 that are used by state machine 246 to monitor differences in sensor data 252 for each of polymer sensor 212 and CO sensor 214. Accordingly, each monitored sensor may independently trigger the air quality anomaly indication.

In the example of FIG. 3, state machine 246 has three states: clean air state 302, anomalous behavior state 304, and anomaly detected state 306. The following description illustrates operation of state machine 246 for polymer sensor 212, and state data 280, and cyclic buffer 254(1), but may equally apply to other ones of sensors 210, others state data 280, and other cyclic buffers 254.

State 288 is initialized to clean air state 302. At intervals, detector firmware 240 reads polymer sensor 212, invokes smoothing algorithm 242 to generate smoothed sensor data 243, and stores smoothed sensor data 243 at head 256(1) of cyclic buffer 254(1), advancing head 256(1) and tail 258(1) accordingly. Detector firmware 240 then invokes anomaly detector 244 to compute difference 270 of smooth sensor data 243 to sensor data 252(1) at tail 258(1) of cyclic buffer 254(1). Difference 270 thereby indicates the smoothed change detected by polymer sensor 212 over the last five-minutes. When state 288 indicates clean air state 302, condition 310 is triggered when difference 270 is greater than a first threshold 282. Condition 310 sets state 288 to anomalous behavior state 304 (e.g., causes state machine 246 to transition to anomalous behavior state 304) and stores the current time, read from real-time clock 207, in timestamp 284. When difference 270 is less than first threshold 282, state machine 246 remains at clean air state 302. State machine 246 then exits until invoked by anomaly detector 244 to process subsequently determined sensor data 252(1).

When state 288 indicates anomalous behavior state 304, condition 320 is triggered when difference 270 is less than second threshold 286. Condition 320 sets state 288 to clean air state 302. For example, where difference 270 does not indicate the required slope, state machine 246 returns to clean air state 302. When state 288 indicates anomalous behavior state 304, condition 330 is triggered when difference 270 is greater than second threshold 286. Condition 330 sets state 288 to anomaly detected state 306 and indicates to anomaly detector 244 that an anomaly has occurred for the corresponding sensor.

When state 288 indicates anomaly detected state 306, condition 340 is triggered when difference 270 is less than second threshold 286. Condition 340 sets state 288 to clean air state 302. This may occur because the corresponding sensor senses a reduced level of the chemical in the air, or because the baseline of the corresponding sensor as defined by tail 258 of the corresponding cyclic buffer 254 has increased over time, such that difference 270 reduces below second threshold 286.

When anomaly detector 244 determines that both (a) state 288 corresponding to CO sensor 214 and (b) state 288 corresponding to at least one polymer sensor 212, are both set to anomaly detected state 306, anomaly detector 244 generates an anomaly detected report 272 to include at least module ID 208 and timestamp 284 corresponding to one or more of CO sensor 214 and polymer sensor 212. Anomaly detector 244 then sends anomaly detected report 272 to cloud detection service 150 to indicate the detected anomaly in air quality.

Figure 4:
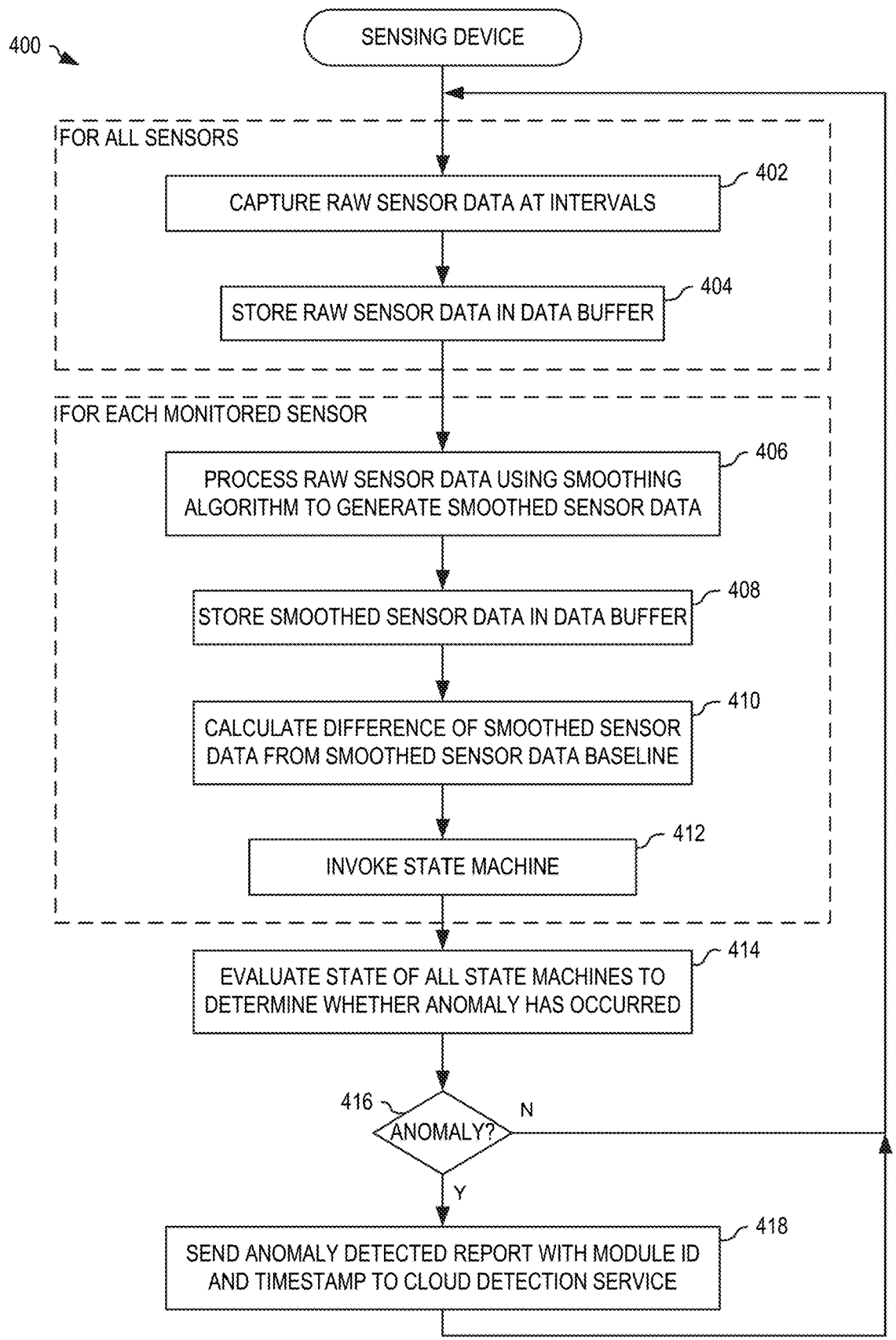
FIG. 4 is a flowchart illustrating one example method for detecting an air quality anomaly in a monitored space, in embodiments.

FIG. 4 is a flowchart illustrating one example method 400 for detecting an air quality anomaly in a monitored space 104. Method 400 is implemented by detector firmware 240 of sensing device 102, for example.

In block 402, method 400 captures raw sensor data at intervals. In one example of block 402, detector firmware 240 uses an internal timer of processor 202 to determine an interval of one second to read raw sensor data from polymer sensor 212. In block 404, method 400 stores raw sensor data in the data buffer. In one example of block 404, detector firmware 240 stores raw sensor data 241 in raw data buffer 260. Blocks 402 and 404 repeat for all sensors 210, reading sensor data and storing it in the raw data buffer.

In block 406, method 400 processes the raw sensor data using a smoothing algorithm to generate smoothed sensor data. In one example of block 406, detector firmware 240 invokes smoothing algorithm 242 to process raw sensor data 241 to generate smoothed sensor data 243. In block 408, method 400 stores the smoothed sensor data in the data buffer. In one example of block 408, detector firmware 240 stores smoothed sensor data 243 at head 256(1) of cyclic buffer 254(1). In block 410, method 400 calculates a difference between the smoothed sensor data and a smoothed sensor data baseline. In one example of block 410, for polymer sensor 212, anomaly detector 244 calculates difference 270 between smooth sensor data 243 and sensor data 252(1) at tail 258(1) of cyclic buffer 254(1). In block 412, method 400 invokes a state machine. In one example of block 412, anomaly detector 244 invokes state machine 246, corresponding to polymer sensor 212, to process difference 270 and update state 288 accordingly. Blocks 406 through 412 repeat for each monitored sensor (e.g., polymer sensor 212 and CO sensor 214).

In block 414, method 400 evaluates the state of all state machines to determine whether an anomaly has occurred. In one example of block 414, anomaly detector 244 evaluates state 288 for each monitored sensor (e.g., polymer sensor 212 and CO sensor 214) and determine that an anomaly has occurred when both (a) state 288 corresponding to CO sensor 214 and (b) state 288 corresponding to at least one polymer sensor 212 are set to anomaly detected state 306. Block 416 is a decision. If, in block 416, method 400 determines that an anomaly has occurred, method 400 continues with block 418; otherwise, method 400 returns to block 402.

In block 418, method 400 sends an anomaly detected report with a module ID and timestamp to cloud detection service. In one example of block 418, anomaly detector 244 generates anomaly detected report 272 and sends it to cloud detection service 150. Method 400 then continues with block 402.

Remote Process Configuration

Each deployed sensing device 102 is configurable from cloud detection service 150 and tracked at a device level. Configurable parameters include: exponential smoothing factors used by smoothing algorithm 242, first and second thresholds 282 and 286 for each monitored sensor 212 and 214, a concurrency duration threshold 290 that defines a period during which sensor readings must exceed both corresponding first and second thresholds 282 and 286, and a consecutive report threshold 292 which defines a minimum amount of time between two reported anomalies. For example, for detection of a smoking anomaly, peaks in values detected by polymer sensor 212 and CO sensor 214 should occur within five minutes of each other, and accordingly, concurrency duration threshold 290 may be set to define a five-minute period. Consecutive report threshold 292 may reduce the number of anomaly detected reports 272 generated by sensing device 102. For example, where a detected anomaly has multiple peaks in sensor values, or where multiple peaks in sensed values are caused by environment cycles, consecutive report threshold 292 may be set to reduce the number of anomaly detected reports 272 sent to cloud detection service 150 for the same event.

Cloud Processing

Sensing device 102 autonomously detects and reports potential anomalies in air quality at monitored space 104. However, sensing device 102 does not identify a likely cause of the anomaly or assess whether there is immediate danger or action needed because of the anomaly. In response to anomaly detected report 272, received in message 110 of FIG. 1 for example, analysis software 156 retrieves and analyzes raw sensor data 260, matching the raw sensor data to profiles of known events affecting air quality, determining whether exposure alert 158 has occurred, and reporting exposure alert 158 to one or more client devices 108 based on the profile match. In certain embodiments, cloud detection service 150 is implemented on a cloud computing platform (e.g., Amazon's Web Service (AWS), or other similar online services). In other embodiments, cloud detection service 150 is implemented using at least one Internet connected server to provide similar functionality. However, for clarity of the following description, only the cloud computing platform solution is described.

Figure 6:
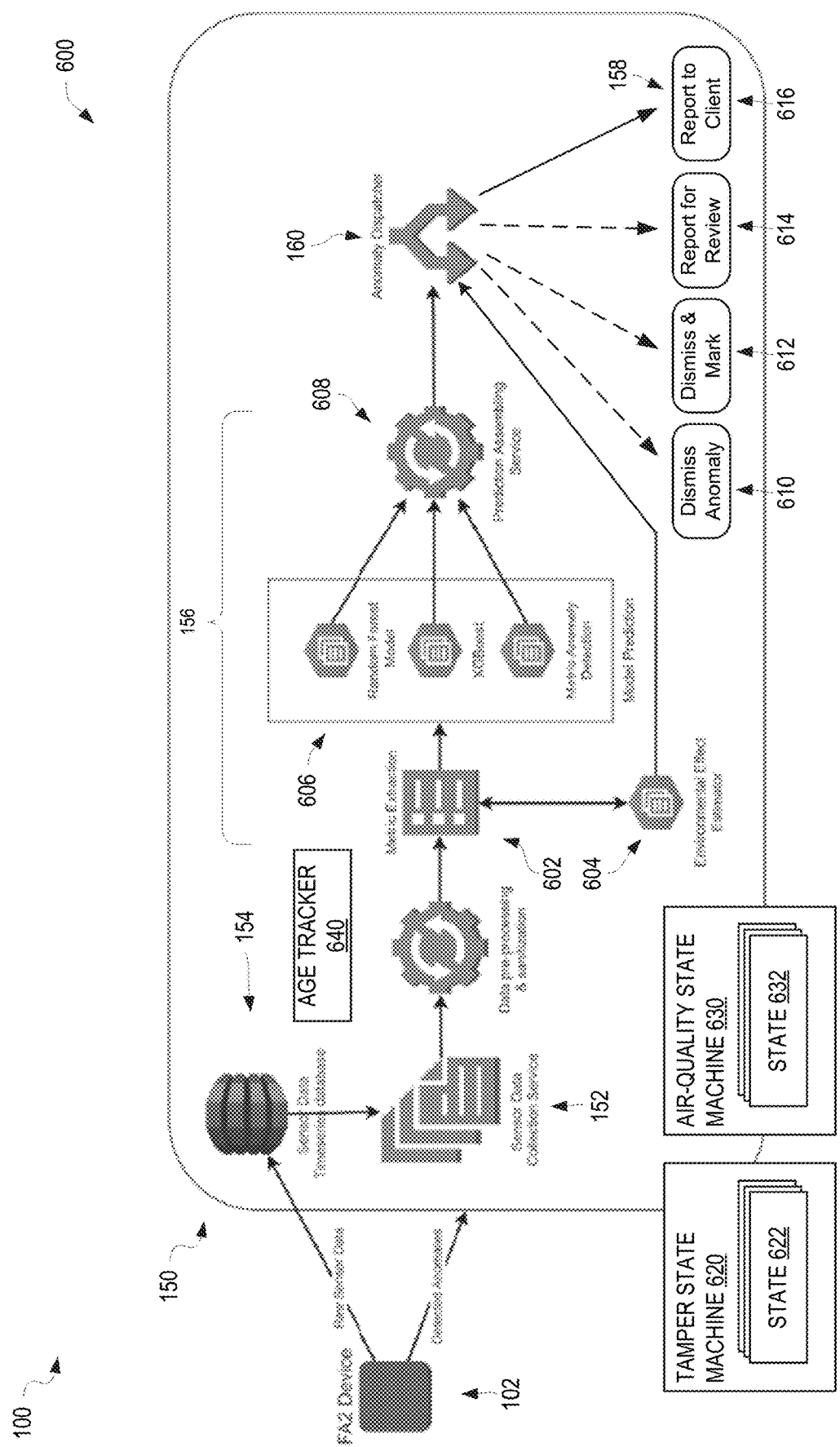
FIG. 6 is a schematic illustrating the system of FIG. 1 with the cloud detection service implemented on a cloud computing platform, in embodiments.

FIG. 6 is a schematic illustrating system 100 of FIG. 1 with cloud detection service 150 implemented on a cloud computing platform 600.

Device Data Aggregation Service

Collection service 152 aggregates data for cloud computing platform 600 by interacting with each deployed sensing device 102 to receive raw sensor data. In certain embodiments, when collection service 152 receives anomaly detected report 272 from sensing device 102, collection service 152 retrieves raw sensor data from the raw data buffer 260. For example, collection service 152 may retrieve the latest forty-five minutes' worth of raw sensor data of each sensor 210 of sensing device 102 in response to receiving anomaly detected report 272. Sensing device 102 sends raw sensor data for all sensors 210, regardless of state 288. Collection service 152 stores the raw sensor data in database 154, which may be implemented as a time series database (e.g., AWS Timestream).

In other embodiments, collection service 152 receives raw sensor data from sensing device 102, at intervals or as captured, and stores the raw sensor data in database 154. When collection service 152 receives anomaly detected report 272 from sensing device 102, collection service 152 retrieves raw sensor data corresponding to the reported anomaly from database 154.

Collection service 152 may format the data prior to storing in database 154. Collection service 152 may also handle and report failures, such as when insufficient data is available for processing.

Raw Data Transfer

As noted above, in certain embodiments, collection service 152 of cloud detection service 150 controls when raw sensor data is transferred from sensing device 102 to cloud detection service 150. In these embodiments, raw sensor data is not always sent to cloud detection service 150, but rather, is only sent when requested by collection service 152. In all embodiments, sensing device 102 advantageously operates as an edge device, detecting the air quality anomaly autonomously and communicating the anomaly to cloud detection service 150. Accordingly, cloud detection service 150 only analyzes raw sensor data when sensing device 102 indicates that an anomaly has been detected. This allows system 100 to scale and handle large numbers of deployed sensing device 102, since cloud detections service 150 is only required to process raw sensor data after the anomaly has been reported by the sensing device 102, as compared to other sensor type systems that transfer sensor data continuously for continual cloud processing.

Figure 5:
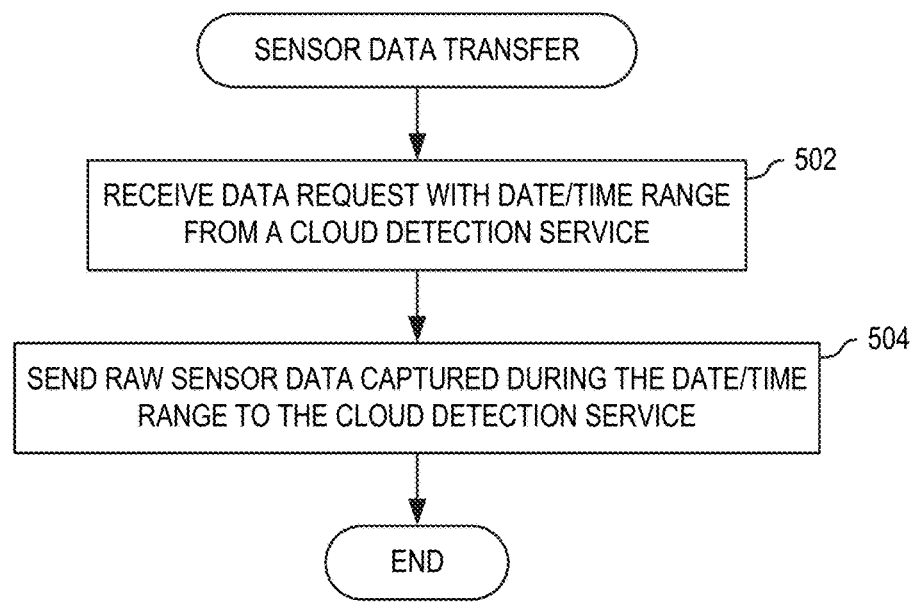
FIG. 5 is a flowchart illustration one example method for transferring raw sensor data to a cloud detection service when requested, in embodiments.

FIG. 5 shows one example method 500 for transferring raw sensor data to cloud detection service 150 when requested. Method 500 is implemented in detector firmware 240 of sensing device 102. In block 502, method 500 receives a data request with a date/time range from a cloud detection service. In one example of block 502, sensing device 102 receives message 162 from cloud base detection service 150 requesting the last forty-five minutes of raw sensor data. In block 504, method 500 sends raw sensor data captured during the date/time range to the cloud detection service. In one example of block 504, detector firmware 240 sends raw sensor data from raw sensor data buffer 260, via interface 206 and using the MQTT protocol over the TCP/IP network, to cloud detection service 150.

Data Preprocessing Service

Collection service 152 may also preprocess the raw data received from sensing device 102 to reduce complexity. This preprocessing may include data smoothing and electrical noise removal using a moving average algorithm, data gap detection and extrapolation, and data normalization.

Collection service 152 may also detect failure of any one of the polymer sensors 212 that is indicated by a long-term baseline being outside a valid operational baseline range (e.g., defined by a low threshold and a high threshold based on a type of the sensor). Data from one or more of the sensors 210 is processed through a smoothing algorithm (e.g., an exponential smoothing algorithm) that determines the long-term baseline for that sensor. The smoothing algorithm is configured to prevent temporary spikes (e.g., caused by a detected event or caused by a temporary environmental change) from indicating failure of the polymer sensor 212. When the long-term baseline is outside the valid operational baseline range of the sensor, failure of the sensor is automatically reported to a customer support team (e.g., via slack), allowing the customer support team to notify the client of the failure and ship a replacement sensor. Particularly, the baseline of polymer sensor 212 and CO sensor 214 may drift with age, and when the baseline is outside the operational baseline range for that type of sensor, the data from the sensor become less reliable. Advantageously, the sensor failure is detected and the customer may be supported by providing a replacement sensor.

In certain embodiments, a rapid change in the baseline value may indicate that the customer has replaced the sensor. For example, analysis software 156 may detect when the long-term baseline, calculated using the exponential smoothing algorithm, quickly drops by a significant amount (e.g., defined by a replacement threshold value), and may detect a gap in the data received from the corresponding sensing device 102 around the time of the sudden drop. Analysis software 156 may thereby determine that the sensing device 102 has been unplugged and that the sensor has been replaced, causing the rapid/abrupt shift in the sensor baseline and the missing data. Advantageously, by detecting when one of the sensors 210 within sensing device 102 has been replaced (e.g., by a customer or service personnel), sensor replacement is simplified overall, since the customer, or the service personnel, are not required to notify the cloud detection service 150 when doing so. By detecting both sensor failure, and sensor replacement, performance of sensing device 102 is guaranteed, and sensor inventory may be controlled automatically, thereby providing full support to customers.

Parametrization and Metric Extraction Service

Analysis software 156 is implemented using several services of cloud computing platform 600, shown in FIG. 6. A metric extraction service 602 transforms the preprocessed data from its time series representation to a one-by-X matrix where each column represents a parameter of the original data. Metric extraction service 602 thereby reduces the dimensionality of the preprocessed raw sensor data in preparation for analysis using machine learning models by providing data that is independent of intrinsic sensor behavior. In machine learning parametrization is needed for the following reasons: data simplification, training speed, and to provide a more generic and/or specialized solution. For example, designing and interpreting results is simplified by removing long terms drift and/or sensing noise from the raw sensor data prior to analysis. This may be accomplished using, for each sensor, a baseline represented by two explicit values: baseline level and a noise magnitude. Advantageously, the machine learning models are then not expected to extract understanding from the raw sensor data that include drift and noise. This data simplification further reduces the time it takes to train and evaluate the machine learning models. Data being input to machine learning models is required to meet strict criteria and thus data compromised by the monitoring environment (e.g., Wi-Fi network issues, power surges, etc.) cannot be used successfully. Accordingly, cloud detection service 150 is designed to be sufficiently robust to yield accurate prediction when parts of the raw data are missing or invalid. Accordingly, metric extraction service 602 prepares the raw sensor data by removing long term drift and/or sensing noise, interpolating to fill gaps in the raw sensor data, and thereby overcoming many data integrity issues that occur in the monitored environment.

Metric extraction service 602 may compute the following key parameters: polymer sensor and CO sensor baselines, normalized polymer sensor and CO sensor response magnitude, polymer sensor and CO sensor response rise time, polymer sensor and CO sensor response recovery level and time, concurrent CO, relative humidity and temperature response magnitude, maximum relative humidity and temperature changes around anomaly, correlation between the polymer sensor and CO sensor responses, correlation between the first derivative of the polymer sensor and CO sensor responses, short term deviation metric, offset magnitude between polymer sensor and CO sensor start, peak and recovery timestamps, and inflection magnitude at the anomaly start timestamp for all sensors.

Environmental Effect Estimation

In addition to the parameters computed above, an environmental effect estimator 604 computes a special metric that captures how much relative humidity or temperature explains the changes observed around the anomaly. This metric is computed using a Random Forest algorithm trained on alert data labeled by whether they were caused by relative humidity, temperature, or smoking.

Model Prediction

Analysis software 156 may also use a model prediction service 606 of cloud computing platform 600. Using the computed parameters and metrics, model prediction service 606 determines a likely cause of the air quality anomaly. Model prediction service 606 is configured with two types of model: a first model implements a machine learning algorithm and a second model implements a manually designed decision tree. The machine learning algorithm may include a Random Forest and Extreme Gradient Boosting Algorithm that are trained using a data set labelled by result (e.g., whether the air quality anomaly was caused by smoking or not). After training, each model returns a prediction on whether the sensor data for the detected air quality anomaly matches a profile of a particular cause. The manually designed decision tree is a model that returns a score between 0 and 10 based on an empirical understanding of interplay between the computed parameters and metrics and a known air quality event (e.g., smoking). This score may also be input to one or more of the above machine learning algorithms and may be used by anomaly dispatcher 160.

Prediction Assembling and Anomaly Dispatching

Analysis software 156 also uses a prediction assembling service 608 of cloud computing platform 600. Prediction assembling service 608 is a last step of analysis software 156 that aggregates the scores from model prediction service 606 and returns a single score indicative of which action should be taken for the identified air quality anomaly. The score is used by anomaly dispatcher 160 to determine which one of four different actions to take: dismiss the anomaly 610, dismiss anomaly and mark for manual review 612, report anomaly for manual review 614, and report anomaly to client 616.

A low score received from prediction assembling service 608 indicates that the first action 610 to dismiss the anomaly should be followed. For example, the model prediction service 606 matches the computed parameters and metrics to a profile cause by relative humidity or temperature changes or by irregular sensor behavior, and which is known to not be an air quality event of concern.

A low to medium score received from prediction assembling service 608 indicates that the second action 612 to dismiss anomaly and mark for manual review should be followed because the model matching is inconclusive. For example, where the computed parameters and metrics do not match any known profile because they have irregular metric values, they do not match a profile of a known air quality event and therefore the air quality anomaly is dismissed. However, anomaly dispatcher 160 marks the sensor data, computed parameters, and/or metrics for review and correct labelling (e.g., whether the data indicate an air quality event or not) later.

A medium to high score received from prediction assembling service 608 indicates that the third action 614 to report anomaly for manual review should be followed. For example, the predicted likelihood of an air quality event is high enough that the event is likely, but fails to meet the high standards required to automatically report the air quality event to the client. Accordingly, anomaly dispatcher 160 generates a report (e.g., exposure alert 158) and marks it for review by a trained agent/operative who will decide on whether to report the air quality event to the client or not.

A high score received from prediction assembling service 608 indicates that the fourth action 616 to report anomaly to client should be followed. For example, the computed parameters and metrics match a known profile that is indicative of an air quality event that should be reported to the client. In another example, when the score is not high enough to indicate a strong profile match but the computed parameters and metrics are within a range of strict thresholds empirically selected to eliminate false positives, the air quality event is reported to the client.

Figure 7:
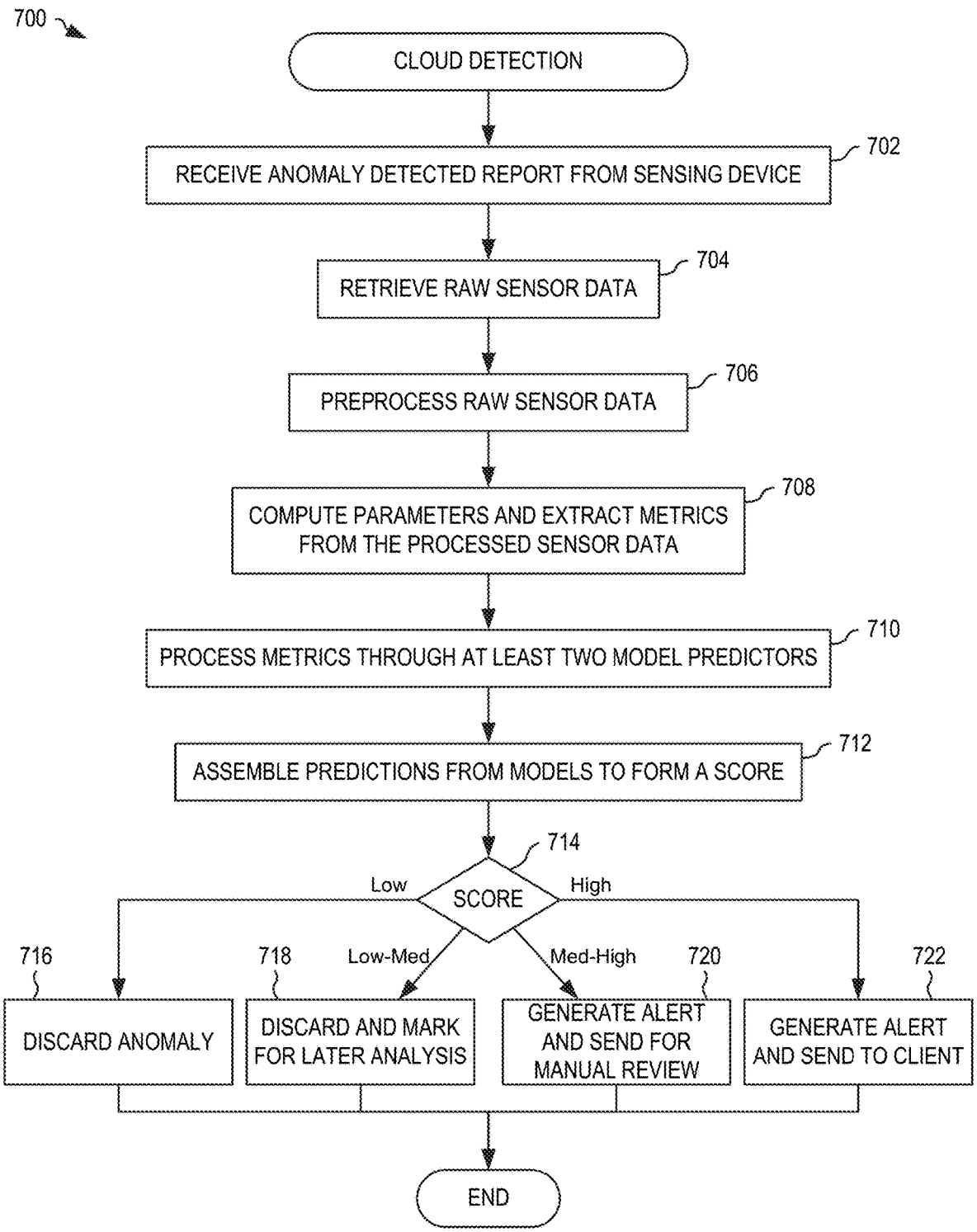
FIG. 7 is a flowchart illustrating one example cloud detection method, in embodiments.

FIG. 7 is a flowchart illustrating one example cloud detection method 700. Method 700 is implemented in collection service 152, analysis software 156, and anomaly dispatcher 160 of cloud detection service 150.

In block 702, method 700 receives an anomaly detected report from a sensing device. In one example of block 702, collection service 152 receives anomaly detected report 272 in message 110 from sensing device 102. In block 704, method 700 retrieves raw sensor data. In one example of block 704, where raw sensor data is not transferred continually or at intervals to cloud detection service 150, collection service 152 sends message 162 to sensing device 102 to request the last forty-five minutes worth of raw sensor data. In another example of block 704, where raw sensor data is transferred continually or at intervals to cloud detection service 150, collection service 152 retrieves the last forty-five minutes worth of raw sensor data from database 154. In block 706, method 700 preprocesses the raw sensor data. In one example of block 706, collection service 152 preprocesses the retrieved raw sensor data using one or more of data smoothing and electrical noise removal using a moving average algorithm, data gap detection and extrapolation, and data normalization. In block 708, method 700 computes parameters and extracts metrics from the preprocessed sensor data. In one example of block 708, metric extraction service 602 transforms the preprocessed data from its time series representation to a one-by-X matrix where each column represents a parameter of the original data.

In block 710, method 700 processes the parameters and metrics through at least two model predictors. In one example of block 710, model prediction service 606 determines a likely cause of the air quality anomaly based upon the parameters and metrics by using two types of model: a first model implements a machine learning algorithm and a second model implements a manually designed decision tree. In block 712, method 700 assembles predictions from models to form a score. In one example of block 712, prediction assembling service 608 aggregates the scores from model prediction service 606 and returns a single score indicative of which action should be taken for the identified air quality anomaly.

Block 714 is a decision. If, in block 714, method 700 determines that the score is at or below a low threshold, method 700 continues with block 716. If, in block 714, method 700 determines that the score is between the low threshold and a medium threshold, method 700 continues with block 718. If, in block 714, method 700 determines that the score is between the medium threshold and a high threshold, method 700 continues with block 720. If, in block 714, method 700 determines that the score is at or higher than the high threshold, method 700 continues with block 722.

In block 716, method 700 discards the anomaly. In one example of block 716, anomaly dispatcher 160 discards the air quality anomaly since it is insignificant. Method 700 then terminates until a subsequent anomaly detected report 272 is received.

In block 718, method 700 discards the anomaly and marks the raw sensor data for later analysis. In one example of block 718, anomaly dispatcher 160 discards the air quality anomaly but marks the received raw sensor data and corresponding parameters and metrics for later analysis. Method 700 then terminates until a subsequent anomaly detected report 272 is received.

In block 720, method 700 generates an air quality alert and flags the alert for manual review. In one example of block 720, anomaly dispatcher 160 generates exposure alert 158 and marks it for review by a trained agent/operative who will decide on whether to report the air quality event to the client or not. Method 700 then terminates until a subsequent anomaly detected report 272 is received.

In block 722, method 700 generates an alert and sends it to the client. In one example of block 722, anomaly dispatcher 160 generates exposure alert 158 and sends it to client device 108 associated with the sensing device 102. Method 700 then terminates until a subsequent anomaly detected report 272 is received.

Tamper Detection

Figures 8, 9:
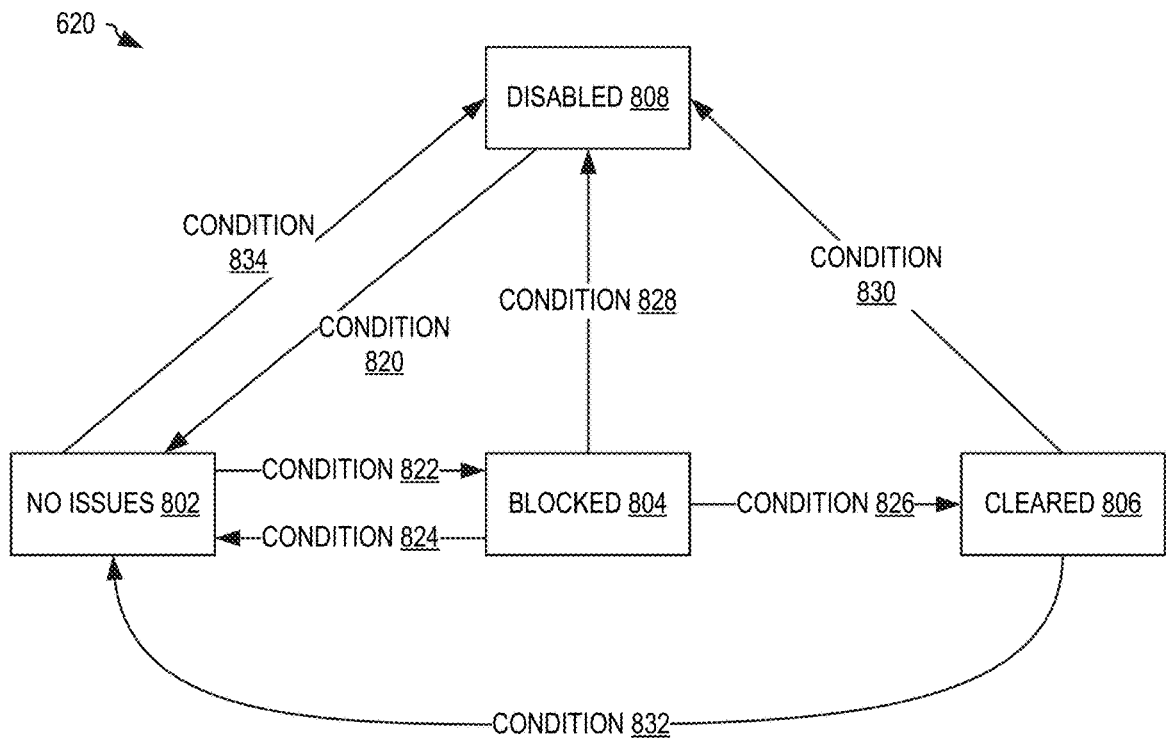
FIG. 8 is a schematic diagram illustrating one example tamper detection state machine, in embodiments.
FIG. 9 shows one example alert screen presented to the user on the client device, in embodiments.

System 100 may also detect tampering of any sensing device 102. Tampering is most likely to involve blocking of airflow into, out of, and around sensing device 102. FIG. 8 is a schematic diagram illustrating one example tamper detection state machine 620. In certain embodiments, tamper detection state machine 620 is implemented by analysis software 156 of cloud detection service 150. In other embodiments, tamper detection state machine 620 is implemented by collection service 152 of cloud detection service 150. As described above, sensing device 102 includes proximity/light sensor 220 that generates a proximity value (e.g., a sensor output) corresponding to blockage of sensing device 102. For example, proximity/light sensor 220 generates a low value when sensing device 102 is being blocked or restricted, and a high value when sensing device 102 is unblocked and able to operate normally. In another example, proximity/light sensor 220 generates a proximity value of between zero and fifty to indicate that sensing device 102 is blocked and generates a proximity value greater than sixty to indicate that no blockage is detected.

As shown in FIG. 6, cloud computing platform 600 may implement tamper detection state machine 620 using a current tamper state 622 (one for each sensing device 102) to track tampering of each sensing device 102. Current tamper state 622 is updated based on proximity values read from proximity/light sensor 220. Tamper state machine 620 has four states: no-issues state 802, blocked state 804, cleared state 806, and disabled state 808. Tamper state 622 is initialized to disabled state 808, and a condition 820 occurs to change tamper state 622 to no-issue state 802 when tamper detection is enabled for sensing device 102. For example, condition 820 may be triggered after sensing device 102 is installed, configured, and made operational.

Raw sensor data from proximity/light sensor 220 is received by collection service 152 and averaged over a five-minute period to generate proximity levels. When in no-issues state 802, a condition 822 occurs when the calculated proximity level is still less than a low proximity threshold (e.g., a value of fifty) at the end of a first duration (e.g., a period of thirty minutes) after the proximity level first dropped below the low proximity threshold. Condition 822 causes tamper state 622 to change to blocked state 804. When transitioning to blocked state 804, analysis software 156 sends an alert to client device 108 of a user of the corresponding sensing device 102. FIG. 9 shows one example alert screen 900 presented to the user on client device 108 for example.

When in blocked state 804, a condition 824 occurs when the calculated proximity level is still larger than a high proximity threshold (e.g., a value of sixty) at the end of a second duration (e.g., a period of ten minutes) after the proximity level first rose above the high proximity threshold. Condition 824 causes tamper state 622 to change to no-issues state 802. When transitioning to no-issues state 802, analysis software 156 clears the blocked flag corresponding to the sensing device 102 in database 154.

Figures 10, 11:
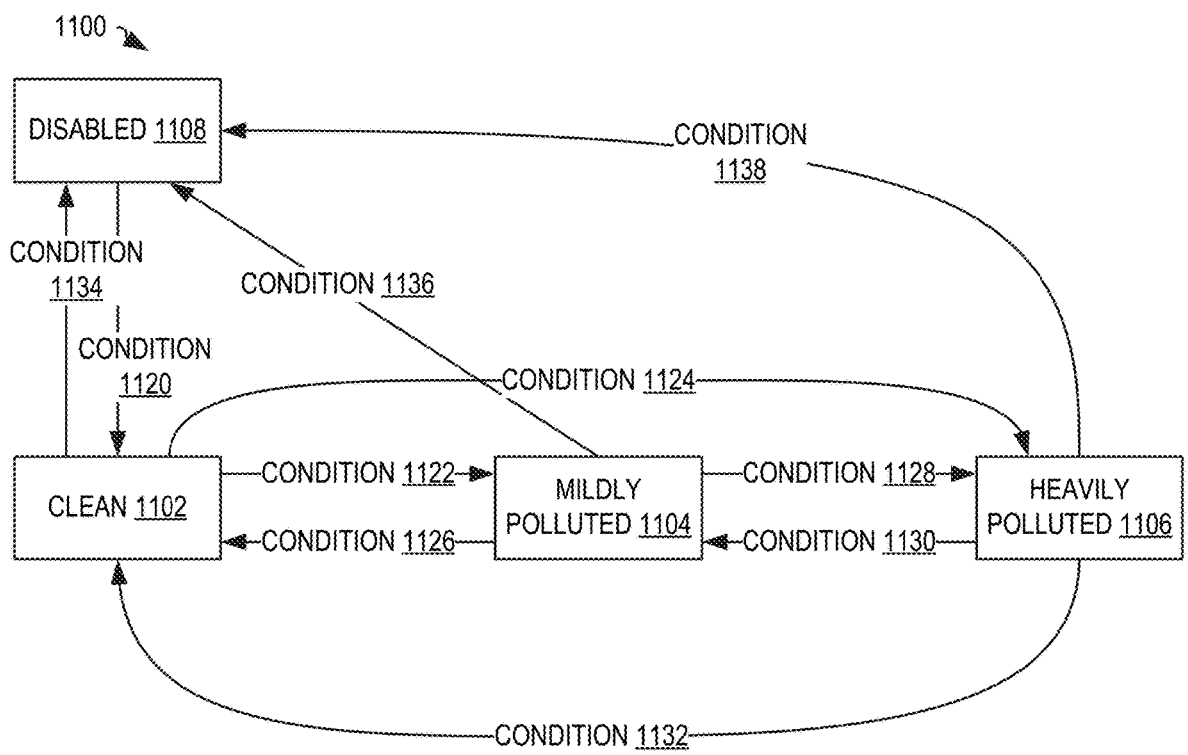
FIG. 10 shows one example "blocked devices" report presented to the user on the client device, in embodiments.
FIG. 11 shows one example air-quality state machine for determining air-quality sensed by the sensing device of FIG. 1, in embodiments.

When in blocked state 804, a condition 826 occurs when a user presses clear on a feedback form, such as when viewing a "Blocking Alert Report" 1000, as shown in FIG. 10, on client device 108. For example, after receiving the alert 900 from analysis software 156 indicating that one sensing device 102 is blocked, the user of the sensing device 102 may clear the alerts by selecting the edit button 1002 within block devices report 1000, and selecting a clear button (not shown) that generates condition 826. Condition 826 causes tamper state 622 to change to clear state 806. When transitioned to the cleared state 806, no further tampering alerts 900 are generated for the corresponding sensing device 102, since the user is aware of the problem.

When in blocked state 804, a condition 828 is triggered when the user disables the sensing device 102. For example, in response to receiving the alert, the user may disable the sensing device 102, for example when maintenance is being performed in the space containing the sensing device 102. When in cleared state 806, a condition 830 causes the tamper state 622 to change to the disabled state 808. For example, the user may disable the sensing device 102 when maintenance is being performed in the space containing the sensing device 102.

When in cleared state 806, a condition 832 occurs when the calculated proximity level is still larger than the high proximity threshold (e.g., a value of sixty) at the end of a third duration (e.g., a period of thirty minutes) after the proximity level first rose above the high proximity threshold. When transitioning to no-issues state 802, analysis software 156 clears the blocked flag corresponding to the sensing device 102 in database 154.

When in no-issues state 802, a condition 834 occurs when the user disables the sensing device 102. For example, the user may disable the sensing device 102 when the space containing the sensing device 102 is to receive maintenance and sensing device 102 will be covered for protection.

Air Quality Monitoring

System 100 may also provide an air quality indication and generate alerts based on air quality sensed by sensing device 102. FIG. 11 shows one example air-quality state machine 630 for determining air-quality sensed by sensing device 102.

In certain embodiments, state machine 630 is implemented by analysis software 156 of cloud detection service 150. In other embodiments, state machine 630 is implemented by collection service 152 of cloud detection service 150. As described above, sensing device 102 includes a plurality of sensors 210 that may be evaluated to determine air-quality near sensing device 102. For example, an integrated air quality (IAQ) level is calculated as a five-minute average of polymer sensor 212, CO sensor 214, VOC sensor 216, and temperature/RH/Pressure sensor 218. In certain embodiments, an integrated circuit incorporates one or more of polymer sensor 212, CO sensor 214, VOC sensor 216, and temperature/RH/Pressure sensor 218 and generates the IAQ level directly. For example, an integrated circuit manufactured by Bosch® uses a proprietary process to generate the IAQ level and provides a mapping of output values to EPA standards. An IAQ level of one-hundred or less indicates clean air. An IAQ level between one-hundred and two-hundred and thirty indicate mildly-polluted air, and an IAQ level greater than two-hundred and thirty indicates heavily-polluted air.

As shown in FIG. 6, cloud computing platform 600 may implement air-quality state machine 630 using a current air-quality state 632 (one for each sensing device 102) to track air-quality at each sensing device 102. Current air-quality state 632 is updated based on the IAQ level determined from one or more of sensors 210. Air-quality state machine 630 has four states: clean state 1102, mildly-polluted state 1104, heavily-polluted state 1106, and disabled state 1108. Air-quality state 632 is initialized to disabled state 1108, and a condition 1120 occurs to change air-quality state 632 to clean state 1102 when air-quality monitoring is enabled for sensing device 102. For example, condition 1120 may be triggered after sensing device 102 is installed, configured, and made operational.

When in clean state 1102, a condition 1122 occurs when the calculated IAQ level is above a first low-pollutant threshold (e.g., a value of one-hundred) at the end of a first duration (e.g., a period of ninety minutes) after the IAQ level first increased above the first low-pollutant threshold. Condition 1122 causes air-quality state 632 to change to mildly-polluted state 1104. When transitioning to mildly-polluted state 1104, analysis software 156 may send an alert to client device 108 of a user of the corresponding sensing device 102. FIG. 12 shows one example mildly-polluted alert screen 1200 presented to the user on client device 108 for example.

When in clean state 1102, a condition 1124 occurs when the calculated IAQ level is above a first high-pollutant threshold (e.g., a value of two-hundred and thirty) at the end of a first duration (e.g., a period of ninety minutes) after the IAQ level first increased above the first high-pollutant threshold. Condition 1124 causes air-quality state 632 to change to heavily-polluted state 1106. When transitioning to heavily-polluted state 1106, analysis software 156 may send an alert to client device 108 of a user of the corresponding sensing device 102. FIG. 13 shows one example heavily-polluted alert 1300 presented to the user on client device 108 for example.

When in mildly-polluted state 1104, a condition 1126 occurs when the calculated IAQ level is still below a second low-pollutant threshold (e.g., a value of ninety) at the end of a first duration (e.g., a period of ninety minutes) after the IAQ level first dropped below the second low-pollutant threshold. The first low-pollutant threshold and the second low-pollutant threshold implement hysteresis. Condition 1126 causes air-quality state 632 to change back to clean state 1102.

When in mildly-polluted state 1104, a condition 1128 occurs when the calculated proximity level is still larger than a first high-pollutant threshold (e.g., a value of two-hundred and thirty) at the end of a first duration (e.g., a period of ninety minutes) after the proximity level first rose above the first high-pollutant threshold. Condition 1128 causes air-quality state 632 to change to heavily-polluted state 1106. When transitioning to heavily-polluted state 1106, analysis software 156 may send heavily-polluted alert 1300 of FIG. 13 to client device 108 of a user of the corresponding sensing device 102.

When in heavily-polluted state 1106, a condition 1130 occurs when the calculated IAQ level is still below a second high-pollutant threshold (e.g., a value of two-hundred) at the end of a first duration (e.g., a period of ninety minutes) after the IAQ level first dropped below the second high-pollutant threshold. The first high-pollutant threshold and the second high-pollutant threshold implement hysteresis. Condition 1130 causes air-quality state 632 to change back to mildly-polluted state 1104.

When in heavily-polluted state 1106, a condition 1132 occurs when the calculated IAQ level is still below the second low-pollutant threshold at the end of a first duration (e.g., a period of ninety minutes) after the IAQ level first dropped below the second low-pollutant threshold. Condition 1132 causes air-quality state 632 to change back to clean state 1102.

When in any of clean state 1102, mildly-polluted state 1104, and heavily-polluted state 1106, a corresponding condition 1134, 1136, and 1138, respectively, occurs when a user disables air-quality monitoring for sensing device 102. Conditions 1134, 1136, and 1138 each cause air-quality state 632 to transition to disabled state 1108. For example, after receiving the heavily-polluted alert 1300 from analysis software 156 indicating that sensing device 102 is experiencing heavily-polluted air, the user may disable air quality monitoring for that sensing device.

Figure 14:
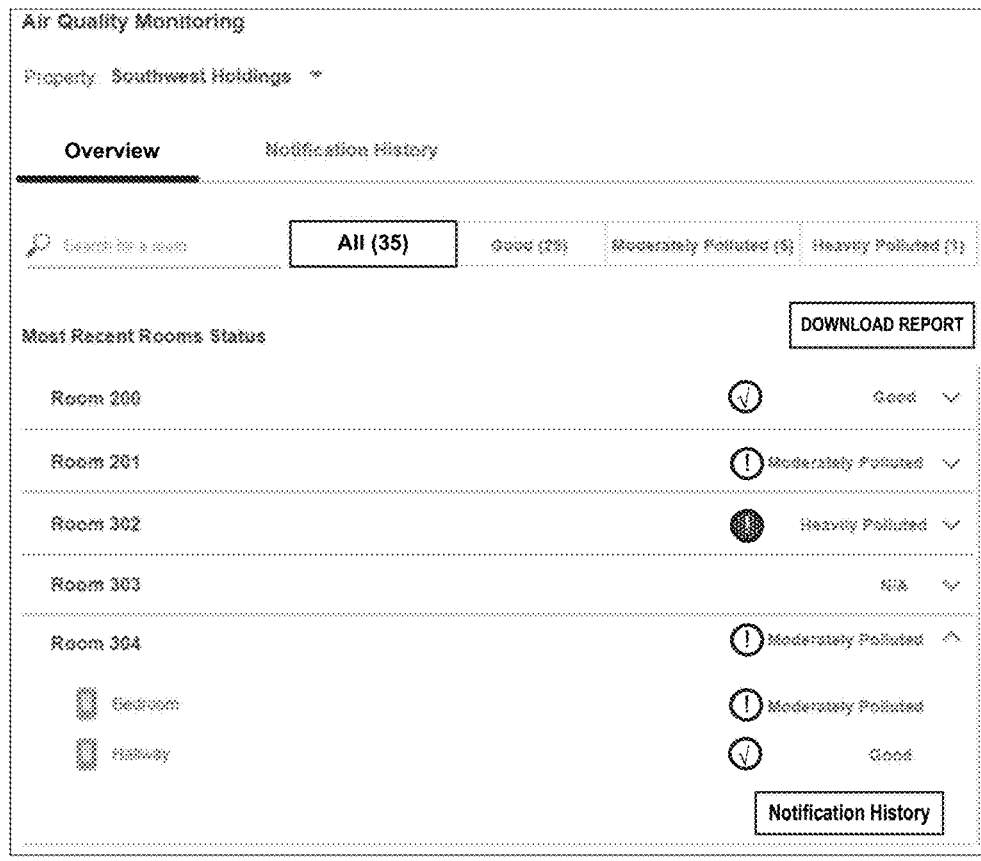
FIG. 14 shows one example air quality monitoring dashboard display providing an overview of air quality for a plurality of sensing devices corresponding to one user, in embodiments.
Figure 15:
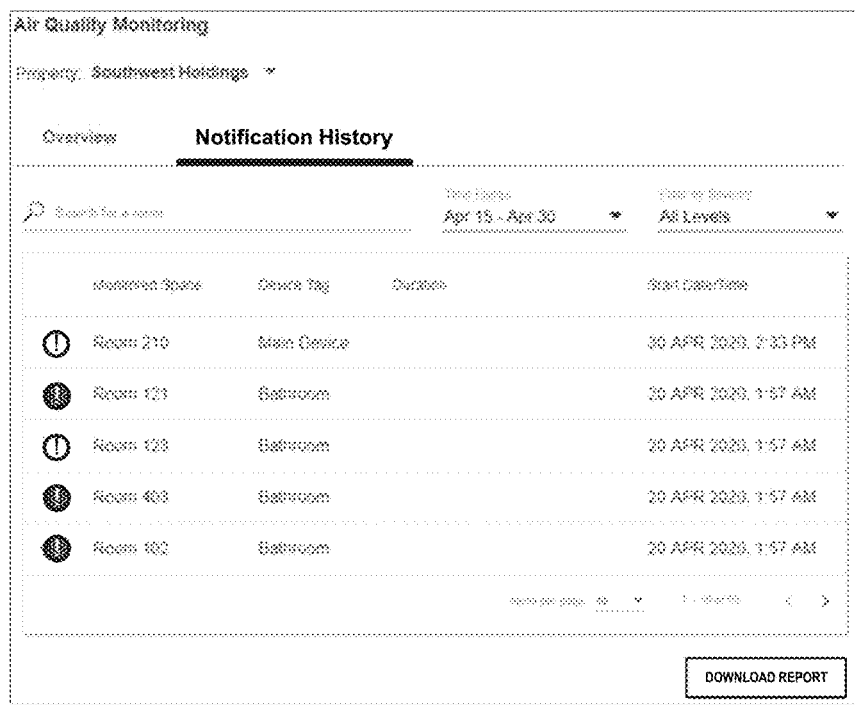
FIG. 15 shows one example air quality monitoring dashboard display providing a history of air quality events for a plurality of sensing devices corresponding to one user, in embodiments.

FIG. 14 shows one example air quality monitoring dashboard display 1400 providing an overview of air quality for a plurality of sensing devices 102 corresponding to one user. Display 1400 provides easily assimilated information on sensed air quality by the sensing devices. FIG. 15 shows one example air quality monitoring dashboard display 1400 providing a history of air quality events for a plurality of sensing devices 102 corresponding to one user. Display 1500 provides easily assimilate information on the air quality history.

Sensor Age Tracking

As described above, polymer sensor 212 and CO sensor 214 may have a finite operational life, where operational viability is indicated by drift in a baseline value of the sensor data. In certain embodiments, cloud detection service 150 includes an age tracker 640 that tracks the age of sensors 210 within sensing device 102. The following examples use polymer sensor 212, however, the same methods and algorithms apply to others of sensors 210.

For example, polymer sensors 212 may have a finite operational life, and system 100 may monitor that life, and schedule a replacement of polymer sensor 212 as needed.

Vaping Detection

Figure 16:
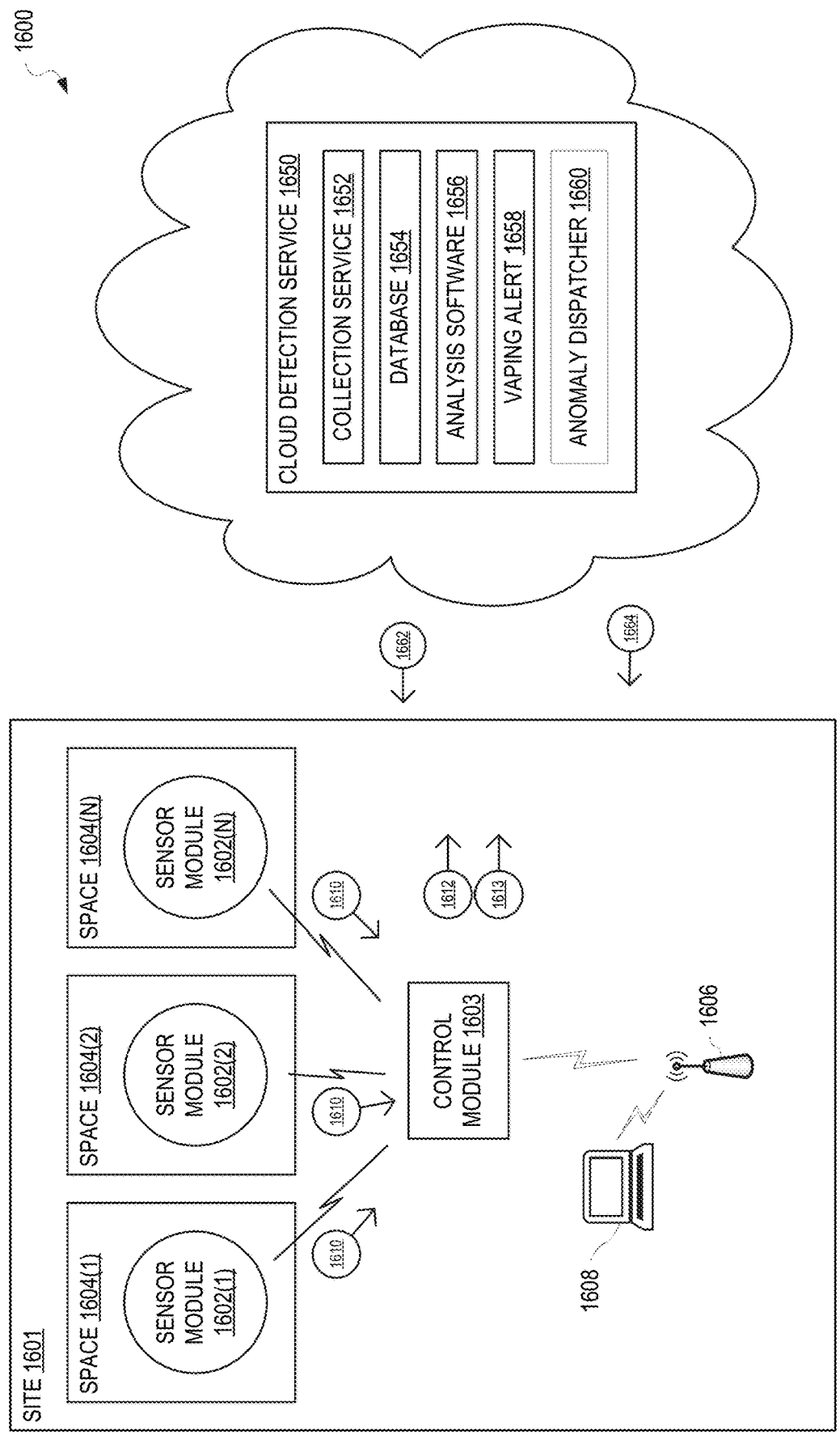
FIG. 16 shows one integrated monitoring and analysis system for detecting vaping, in embodiments.

FIG. 16 shows one example vaping detection system 1600 for detecting the use of an electronic cigarette (e-cigarette) in a monitored space 1604 of a site 1601. E-cigarettes produce an aerosol of a liquid containing an addictive drug (e.g., nicotine or marijuana) for inhalation by a person. System 1600 includes at least one sensor module 1602, a control module 1603 and a cloud detection service 1650. In the example of FIG. 16, site 1601 (e.g., a school) has a plurality of spaces 1604(1)-(N) (e.g., restrooms) where vaping is prohibited, and each space 1604 has one sensor module 1602(1)-(N), respectively. The control module 1603 supports multiple (N) sensor modules 1602 that are within wireless communication range and receives sensor data when any one sensor module 1602 detects vaping. Advantageously, system 1600 is highly scalable and more or fewer sensor modules 1602 and/or more or fewer control modules 1603 may be deployed at a site 1601.

Sensor modules 1602 communicate, using a short-range wireless (or wired) protocol (e.g., one or more of Bluetooth, Zwave, ZigBee, etc.), with control module 1603, which is located near (e.g., within wireless communication range) monitored space 1604. Sensor module 1602 may be battery powered (e.g., not requiring any wiring), small and unobtrusive, allowing it to be installed within an air extraction duct of space 1604.

Control module 1603 communicates with a collection service 1652 (e.g., a communication interface) of cloud detection service 1650 via a local wireless network 1606 using one or more wireless (or wired e.g., Ethernet) protocols, including Wi-Fi, Bluetooth, Zwave, ZigBee, and so on. Local wireless network 1606 may connect to the Internet and thereby allow control module 1603 to communicate with cloud detection service 1650.

Cloud detection service 1650 may include a database 1654 that associates a client device 1608 (e.g., a computer, laptop, tablet, smartphone, etc.) with one or more of site 1601, monitored space 1604, and sensor module 1602. For example, client device 1608 may be used by an administrator or other staff at the school.

Each sensor module 1602(1)-(N) reads sensor data from included sensors (see sensors 1810, FIG. 18) at intervals (e.g., thirty seconds, 1 minute, two minutes, etc.) and sends the sensor data, in a message 1610 identifying itself, to control module 1603. For each sensor module 1602, control module 1603 processes the sensor data to detect vaping within the corresponding monitored space 1604. When the sensor data is indicative of vaping, control module 1603 sends a message 1612 identifying itself and/or sensor module 1602(1)-(N), indicating a time that vaping was sensed, and corresponding sensor data (e.g., raw sensor data collected for a period including the time of detection) to cloud detection service 1650. In certain embodiments, control module 1603 may also send an alert to client device 1608. In other embodiments, in response to message 1612, cloud detection service 1650 sends the alert to client device 1608.

In certain embodiments, each control module 1603 buffers raw sensor data and waits for collection service 1652 to request raw data corresponding to message 1612 reporting the time of the anomaly. For example, collection service 1652 sends a message 1662 to control module 1603 requesting sensor data captured by sensor module 1602, identified in message 1612; and, control module 1603, in response, sends the corresponding sensor data, shown as message 1613, to cloud detection service 1650. In other embodiments, control module 1603 may send raw sensor data at intervals (e.g., as blocks of data) to collection service 1652 as it is received from each sensor module 1602. Accordingly, when control module 1603 sends message 1612 identifying itself, identifying sensor module 1602, and indicating the time of the anomaly to cloud detection service 1650, raw sensor data corresponding to the anomaly has already been received by collection service 1652.

In certain embodiments, control module 1603 may be omitted and sensor module 1602 may be similar to sensing device 102 of FIG. 2, implementing a smoothing algorithm, an anomaly detector, and state machine. In this embodiment, sensor module 1602 communicates directly with cloud detection service 1650 via local wireless network 1606.

Analysis software 1656 of cloud detection service 1650 further analyzes the raw sensor data and generates a vaping alert 1658 based on a determined cause of the air quality anomaly. As described in detail below, analysis software 1656 may use AI algorithms and techniques to analyze raw sensor data captured from at least two different sensors of sensor module 1602 to determine a cause of vaping alert 1658. Analysis software 1656 may implement self-learning to improve analysis and detection of air quality anomalies over time. An anomaly dispatcher 1660 of the cloud detection service 1650 identifies client device 1608 as being associated with monitored space 1604 and sends a message 1664 including vaping alert 1658 to client device 1608.

Figure 17A:
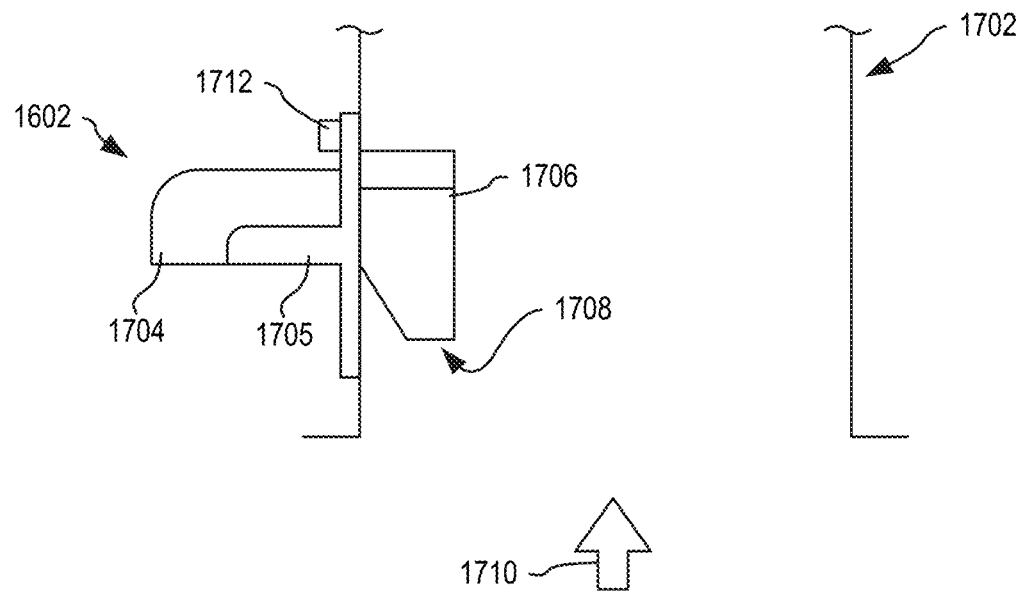
FIG. 17A is a perspective cut-away side view illustrating example positioning of the sensor module of FIG. 16 within an air extraction duct, in embodiments.

FIG. 17A is a cut-away side view illustrating example positioning of sensor module 1602 of FIG. 16 within an air extraction duct 1702. Sensor module 1602 includes a housing that has at least three portions: an electronic housing 1704, a bracket portion 1705, and an airbox 1706. Bracket portion 1705 attaches to air extraction duct 1702 such that airbox 1706 is positioned within air extraction duct 1702. Airbox 1706 is shaped and sized to fit within air extraction duct 1702 without any significant restriction to air flow (indicated by arrow 1710) through the air extraction duct. Bracket portion 1705 may include at least one retaining device 1712 that removably retains bracket portion 1705 with air extraction duct 1702. Airbox 1706 has at least one aperture 1708 (or other similar aperture) that allow air flow 1710, at least in part, to pass over sensors (see poly sensor 1812, VOC sensor 1816, and temp/RH sensor 1818 of FIG. 18) within electronic housing 1704. Sensor module 1602 is easily secured within the air extraction duct 1702 to detect vaping within space 1604. Where space 1604 has multiple air extraction ducts 1702, one sensor module 1602 may be deployed within each air extraction duct 1702. Advantageously, sensor module 1602 may be hidden behind a grill (not shown) of air extraction duct 1702 (e.g., in the ceiling of space 1604) and is therefore not easily detected. Further, sensor module 1602 uses minimal power and may operate for extended periods (e.g., up to one year) before requiring the battery to be replaced, thereby incurring minimal maintenance overhead. To reduce power use and conserver battery power, sensor module 1602 performs minimal processing and communication. For example, sensor module 1602 may have a heartbeat period (e.g., 12 hours, 4 hours, 1 hour, etc.), whereby sensor module 1602 sends a ping to control module 1603 when no other communication has occurred during the heartbeat period. Accordingly, control module 1603 learns that sensor module 1602 has failed when communication has not been received for longer than the heartbeat period. When control module 1603 determines that sensor module 1602 has failed, control module 1603 may send a notification to an operator (e.g., via client device 1608) indicating that sensor module 1602 requires servicing.

Figure 17B:
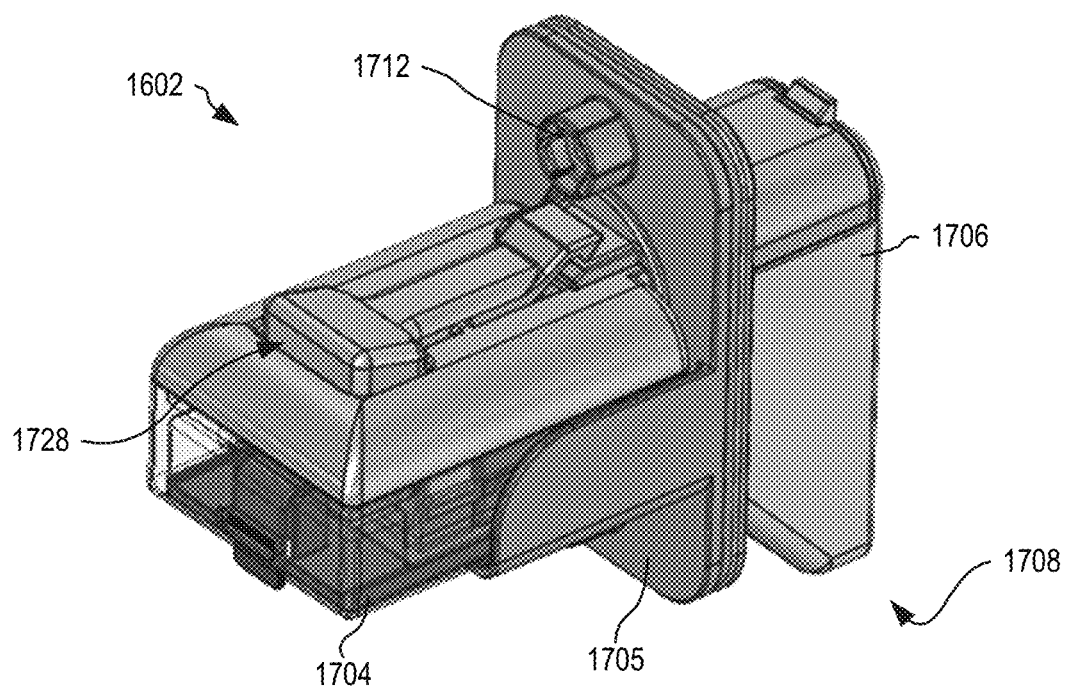
FIG. 17B is a perspective view illustrating sensor module of FIG. 17A in further example detail.

FIG. 17B is a perspective view illustrating sensor module 1602 of FIG. 17A in further example detail. Electronic housing 1704 may include a release mechanism 1728 that removably retains electronic housing 1704 with bracket portion 1705. Release mechanism 1728 allows electronic housing 1704 to be removed from bracket portion 1705, to change one or more of a battery and/or a polymer sensor. Advantageously, bracket portion 1705 may remain attached to air extraction duct 1702 when servicing electronic housing 1704.

Figure 18:
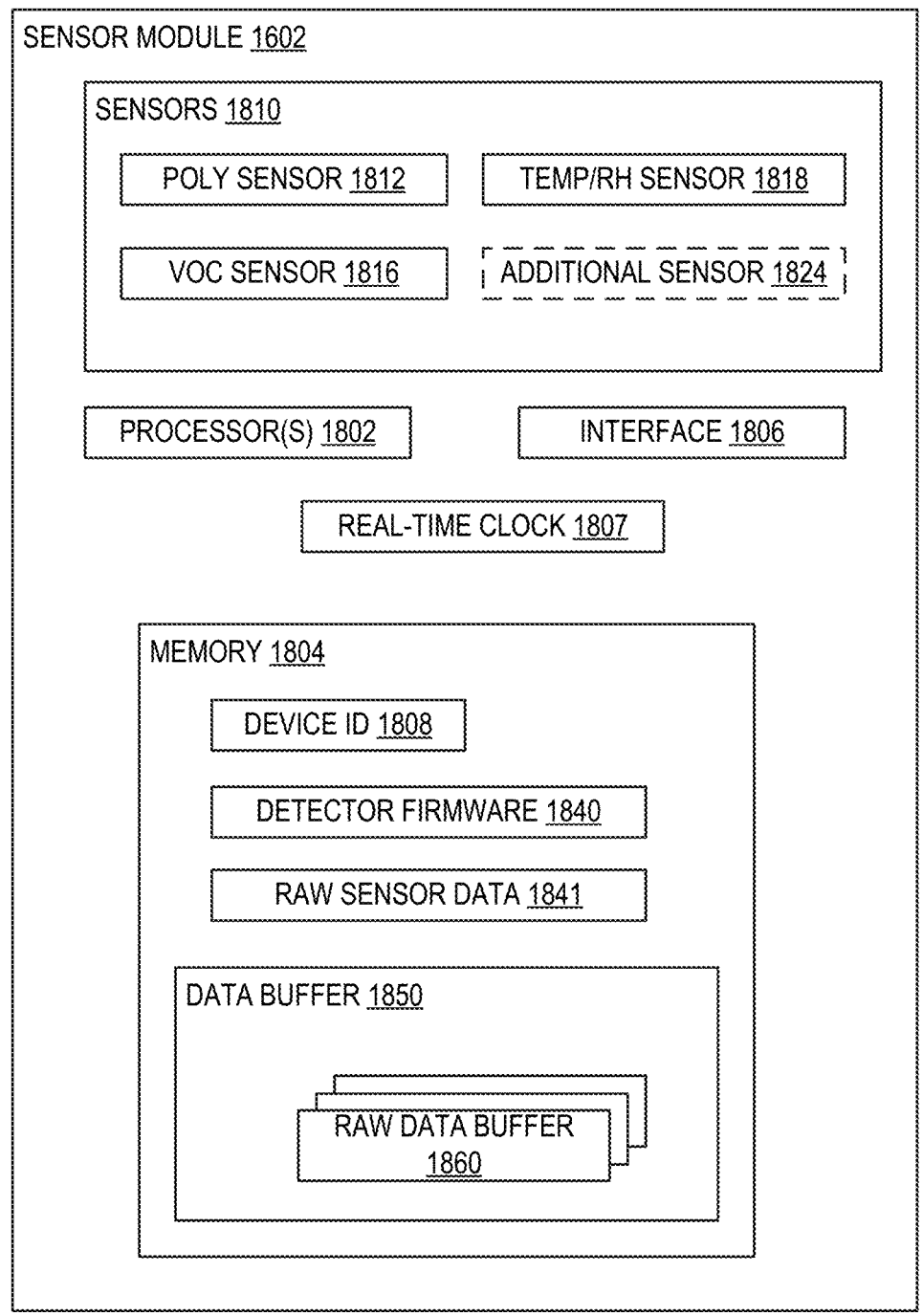
FIG. 18 is a block diagram showing the sensor module of FIG. 16 in further example detail, in embodiments.

FIG. 18 is a block diagram showing sensor module 1602 of FIG. 16 in further example detail. FIGS. 16 and 18 are best viewed together with the following description. In this embodiment, sensor module 1602 does not process raw sensor data, but sends it to control module 1603 for processing. Sensor module 1602 may include a plurality of sensors 1810, including at least one polymer sensor 1812 that senses a level of a targeted molecule in the air, one or more environmental sensors such as a volatile organic compound (VOC) sensor 1816, and a temperature/relative humidity/atmospheric pressure sensor 1818. U.S. patent application Ser. No. 16/656,482 entitled "DIOL AND TRIOL SENSORS AND ASSOCIATED METHODS," filed on Oct. 17, 2019, incorporated herein by reference, provides details of sensors that detect airborne substances produced by vaping. In certain embodiments, sensor module 1602 is configurable to include up to three different types of polymer sensors 1812, each detecting a different environmental pollutant in the ambient air such as one or more of tobacco smoke, marijuana smoke, toxic industrial chemicals, bacteria, etc. The environmental sensors may sense temperature, relative and/or absolute humidity, volatile organic chemical concentration, atmospheric pressure, and so on, and may be used to calibrate the response of the polymer sensor 1812. Sensor module 1602 may include one or more additional sensors 1824 without departing from the scope hereof. Sensors 1810 are positioned, within housing 1704 of sensor module 1602, to experience air flow 1710 via vents 1706/1708. Advantageously, by being positionable to sample air moving through air extraction duct 1702, no additional fan is needed to move air over sensors 1810.

Sensor module 1602 may include at least one processor 1802 communicatively coupled with memory 1804 storing detector firmware 1840 that includes machine-readable instructions which, when executed by processor 1802, cause processor 1802 to implement functionality of sensor module 1602 as described herein. Sensor module 1602 may also include an interface 1806 for communicating with control module 1603 and may include a real-time clock 1807 that maintains a current time and date. Detector firmware 1840 may synchronize, once and/or periodically, real-time clock 1807 to an online time service as known in the art. In other embodiments, detector firmware 1840 may implement and maintain real-time clock 1807 in memory 1804 using software.

Memory 1804 also stores a device ID 1808 that uniquely identifies sensor module 1602 to control module 1603 and to cloud detection service 1650. For example, device ID 1808 may be included within messages sent by sensor module 1602 to control module 1603 and in messages sent from control module 1603 to cloud detection service 1650 such that cloud detection service 1650 attributes the messages and their content to the correct sensor module 1602.

Memory 1804 also includes a data buffer 1850 for storing raw sensor data 1841 read from each sensor 1810. Each raw data buffer 1860 may be a cyclic buffer that stores at least forty-five minutes' worth of raw sensor data 1841 read from one of sensors 1810. However, data buffer 1850 may be sized to store more or less raw sensor data 1841 without departing from the scope hereof.

Detector firmware 1840 reads raw sensor data (shown as raw sensor data 1841 in memory 1804) from at least one of sensors 1810 at intervals (e.g., once per second, once per minute, etc.), and stores the raw sensor data 1841 in the corresponding raw data buffer 1860. For example, detector firmware 1840 may use an internal timer of processor 1802 to determine an interval of one minute between reading of raw sensor data from polymer sensor 1812. Detector firmware 1840 sends raw sensor data from raw data buffers 1860 to control module 1603 for processing.

Figure 19:
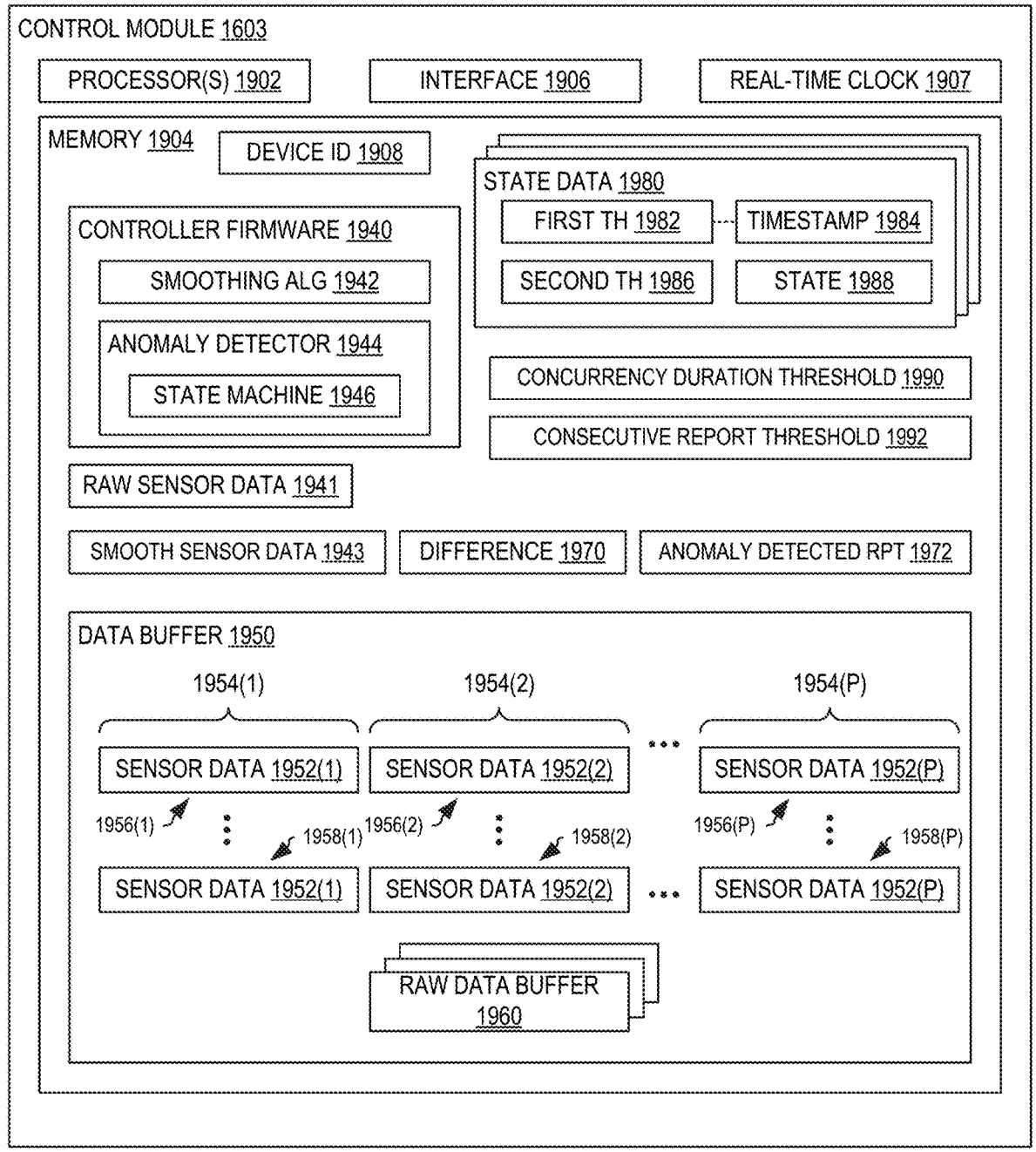
FIG. 19 is a block diagram showing the control module of FIG. 16 in further example detail, in embodiments.

FIG. 19 is a block diagram showing control module 1603 of FIG. 16 in further example detail. In the example of FIG. 19 and the following description, sensor data for one sensor module 1602(1) is shown and described; however, control module 1603 may concurrently independently buffer and independently process sensor data from multiple sensor modules 1602. Control module 1603 includes a processor 1902, an interface 1906, a real-time clock 1907, and memory 1904 storing a device ID 1908 that uniquely identifies control module 1603, and controller firmware 1940 implemented as machine-readable instructions that, when executed by processor 1902, causes processor 1902 to implement functionality of control module 1603 as described herein.

Control module 1603 includes an anomaly detector 1944, implemented as machine-readable instructions of controller firmware 1940, that processes the raw sensor data received from the sensor module 1602 to detect and report a potential vaping event. For each sensor module 1602, control module 1603 may include state data 1980, with first threshold 1982, timestamp 1984, second threshold 1986, and state 1988 that are similar to state data 280, first threshold 282, timestamp 284, second threshold 286, and state 288 of FIG. 2, and that are similarly used by anomaly detector 1944. Memory 1904 also stores concurrency duration threshold 1990, consecutive report threshold 1992, raw sensor data 1941, smooth sensor data 1943, differences 1970, and anomaly detected report 1972 that are similar to concurrency duration threshold 290, consecutive report threshold 292, raw sensor data 241, smooth sensor data 243, differences 270, and anomaly detected report 272 of FIG. 2 and are similarly used by anomaly detector 1944. Memory 1904 also stores a data buffer 1950 with independent cyclic buffers 1954, each having a head pointer 1956 and a tail pointer 1958, that are similar to independent cyclic buffers 254, head pointer 256 and tail pointer 258 of FIG. 2.

Anomaly detector 1944 operates similarly to anomaly detector 244 of FIG. 2 to process the raw sensor data received from each sensor module 1602, invoking smoothing algorithm 1942 to generate smooth sensor data 1943 that is stored in the corresponding independent cyclic buffer 1954, and using state machine 1946 to determine when a potential vaping anomaly is detected. Accordingly, the description of operation of anomaly detector 1944 is not repeated again herein.

Parameters used by anomaly detector 1944 may be configured (e.g., from cloud detection service 1650) to minimize false negatives and cloud detection service 1650, using cloud AI models, reduces false positives. This allows cloud detection service 1650 to collect a wider range of anomalies that may be used to improve detection algorithms and cloud AI models. For example, anomaly detector 1944 sends anomaly detected report 1972 to cloud detection service 1650, which may request raw sensor data corresponding to the anomaly, and perform further analysis thereon to confirm vaping is detected.

Figure 20:
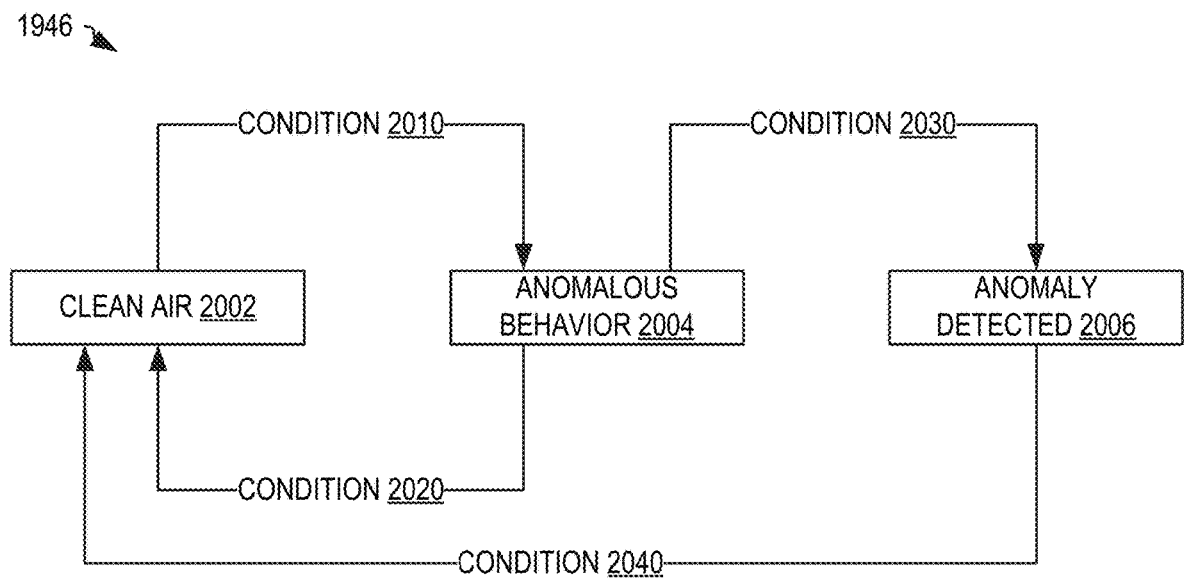
FIG. 20 is a block diagram illustrating example detail of the state machine of FIG. 19, in embodiments.

FIG. 20 is a block diagram illustrating example detail of state machine 1946 of FIG. 19. State machine 1946 is invoked by anomaly detector 1944 to independently monitor at least two different ones of sensors 1810, maintaining, for each monitored sensor, state data 1980 that includes a first threshold 1982 corresponding to the determined difference in sensor data 1952, a timestamp 1984 for storing when the anomaly was detected, a second threshold 1986 corresponding to a second determined difference (e.g., the slope) in sensor data 1952, and a current state 1988 of state machine 1946 for the sensor. Second threshold 1986 may be the same as first threshold 1982, or may be different. First threshold 1982 and second threshold 1986 define a slope that sensor data 1952 is required to indicate for the anomaly in air quality to be reported. First and second thresholds 1982 and 1986 may be selected to eliminate the risk of false negatives while minimizing the number of false positives being reported by sensor module 1602. Continuing with the example of FIG. 18, where sensor module 1602 includes polymer sensor 1812 and VOC sensor 1816, memory 1904 in control module 1603 may store two instances of state data 1980 that are used by state machine 1946 to monitor differences in sensor data 1952 for each of polymer sensor 1812 and VOC sensor 1816. Accordingly, each monitored sensor may independently trigger the air quality anomaly indication.

As shown in FIG. 20, state machine 1946 has three states: clean air state 2002, anomalous behavior state 2004, and anomaly detected state 2006. The following description illustrates operation of state machine 1946 for polymer sensor 1812, and state data 1980, and cyclic buffer 1954(1), but may equally apply to other ones of sensors 1810, others state data 1980, and other cyclic buffers 1954.

State 1988 is initialized to clean air state 2002. When state 1988 indicates clean air state 2002, condition 2010 is triggered when difference 1970 is greater than a first threshold 1982. Condition 2010 sets state 1988 to anomalous behavior state 2004 (e.g., causes state machine 1946 to transition to anomalous behavior state 2004) and stores the current time, read from real-time clock 1907, in timestamp 1984. When difference 1970 is less than first threshold 1982, state machine 1946 remains at clean air state 2002. State machine 1946 then exits until invoked by anomaly detector 1944 to process a subsequently determined sensor data 1952(1).

When state 1988 indicates anomalous behavior state 2004, condition 2020 is triggered when difference 1970 is less than second threshold 1986. Condition 2020 sets state 1988 to clean air state 2002. For example, where difference 1970 does not indicate the required slope, state machine 1946 returns to clean air state 2002. When state 1988 indicates anomalous behavior state 2004, condition 2030 is triggered when difference 1970 is greater than second threshold 1986. Condition 2030 sets state 1988 to anomaly detected state 2006 and indicates to anomaly detector 1944 that an anomaly has occurred for the corresponding sensor.

When state 1988 indicates anomaly detected state 2006, condition 2040 is triggered when difference 1970 is less than second threshold 1986. Condition 2040 sets state 1988 to clean air state 2002. This may occur because the corresponding sensor senses a reduced level of the chemical in the air, or because the baseline of the corresponding sensor as defined by tail 1958 of the corresponding cyclic buffer 1954 has increased over time, such that difference 1970 reduces below second threshold 1986.

When anomaly detector 1944 determines that both (a) state 1988 corresponding to VOC sensor 1816 and (b) state 1988 corresponding to at least one polymer sensor 1812, are both set to anomaly detected state 2006, anomaly detector 1944 generates an anomaly detected report 1972 to include at least module ID 1908 and timestamp 1984 corresponding to one or more of VOC sensor 1816 and polymer sensor 1812. Anomaly detector 1944 then sends anomaly detected report 1972 to cloud detection service 1650 to indicate the detected vaping.

Figure 21:
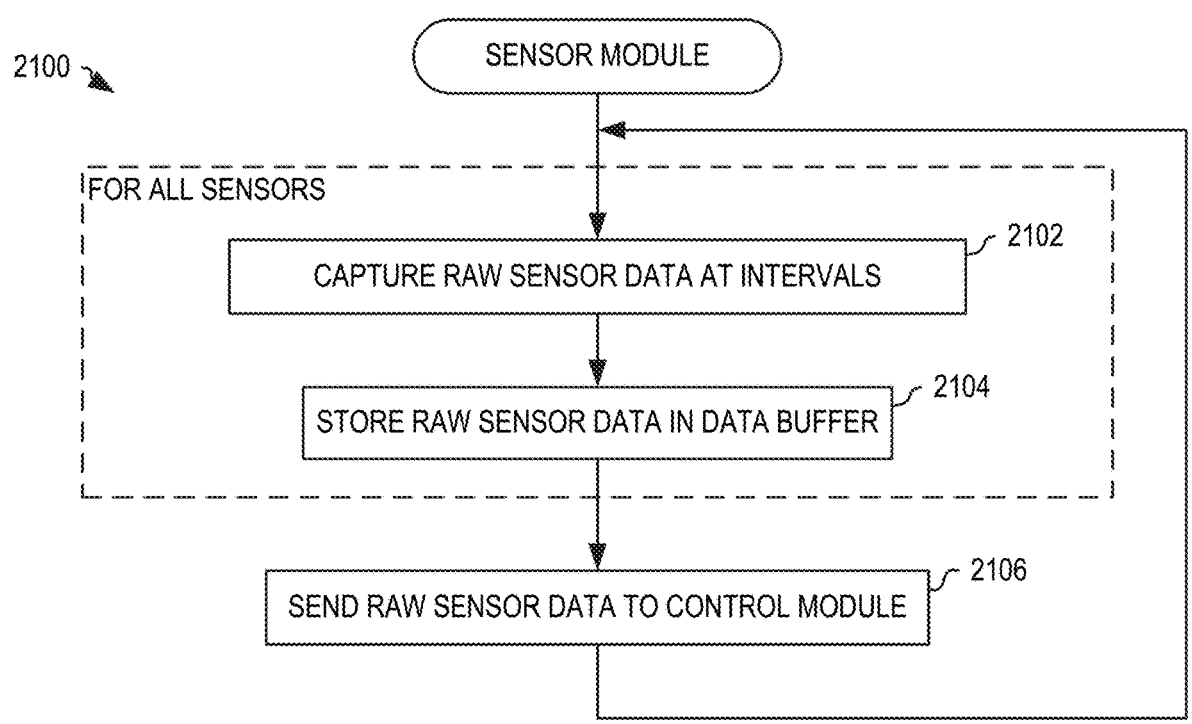
FIG. 21 is a flowchart illustrating one example method for detecting vaping in a monitored space, in embodiments.

FIG. 21 is a flowchart illustrating one example method 2100 for capturing raw sensor data corresponding to a monitored space 1604 and sending the raw sensor data to control module 1603 for further processing. Method 2100 is implemented by detector firmware 1840 of sensor module 1602, for example.

In block 2102, method 2100 captures raw sensor data at intervals. In one example of block 2102, detector firmware 1840 uses an internal timer of processor 1802 to determine an interval of one second to read raw sensor data 1841 from polymer sensor 1812. In block 2104, method 2100 stores raw sensor data in the data buffer. In one example of block 2104, detector firmware 1840 stores raw sensor data 1841 in raw data buffer 1860. Blocks 2102 and 2104 repeat for all sensors 1810, reading sensor data and storing it in the raw data buffer.

In block 2106, method 2100 sends raw sensor data to the control module. In one example of block 2106, sensor module 1602 reads raw sensor data 1841 from raw data buffer 1860 and sends raw sensor data 1841 to control module 1603. Blocks 2102 through 2106 repeat at intervals to read and send sensor data to control module 1603.

Figure 22:
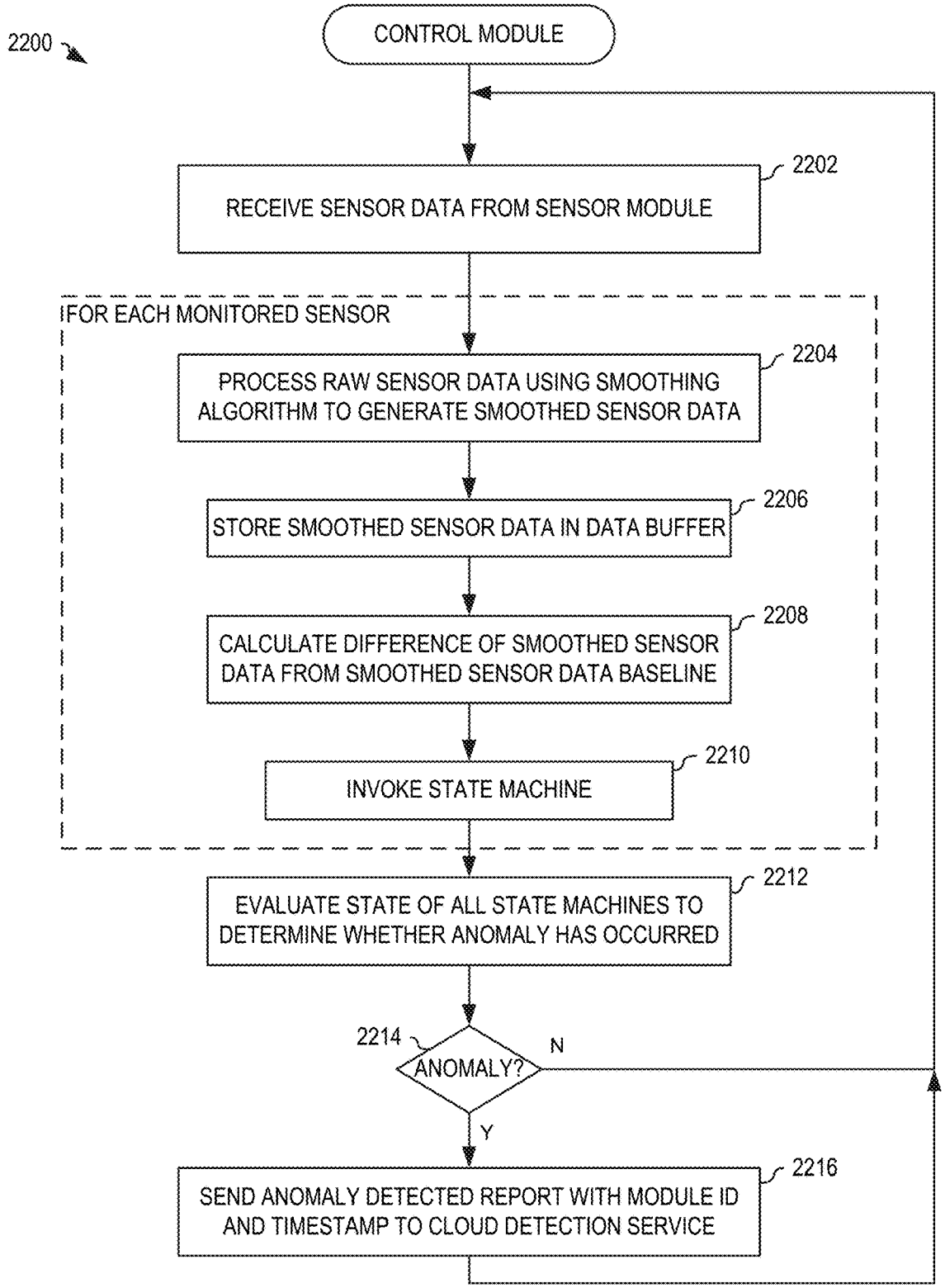
FIG. 22 is a flowchart illustrating one example method for receiving and analyzing raw sensor data from the sensor module to detect vaping, in embodiments.

FIG. 22 is a flowchart illustrating one example method 2200 for receiving and analyzing raw sensor data 1841 from sensor module 1602 to detect vaping. Method 2200 is implemented by controller firmware 1940 of control module 1603, for example.

In block 2202, method 2200 receives raw sensor data from a sensor module. In one example of block 2202, control module 103 receives raw sensor data 1841 from sensor module 1602 using a short-range wireless protocol of interface 1906. In block 2204, method 2200 processes the raw sensor data using a smoothing algorithm to generate smoothed sensor data. In one example of block 2204, controller firmware 1940 invokes smoothing algorithm 1942 to process raw sensor data 1841 to generate smoothed sensor data 1943. In block 2206, method 2200 stores the smoothed sensor data in the data buffer. In one example of block 2206, controller firmware 1940 stores smoothed sensor data 1943 at head 1956(1) of cyclic buffer 1954(1). In block 2208, method 2200 calculates a difference between the smoothed sensor data and a smoothed sensor data baseline. In one example of block 2208, for polymer sensor 1812, anomaly detector 1944 calculates difference 1970 between smooth sensor data 1943 and sensor data 1952(1) at tail 1958(1) of cyclic buffer 1954(1). In block 2210, method 2200 invokes a state machine. In one example of block 2210, anomaly detector 1944 invokes state machine 1946, corresponding to polymer sensor 1812, to process difference 1970 and update state 1988 accordingly. Blocks 2204 through 2210 repeat for each monitored sensor (e.g., polymer sensor 1812 and VOC sensor 1816).

In block 2212, method 2200 evaluates the state of all state machines to determine whether an anomaly has occurred. In one example of block 2212, anomaly detector 1944 evaluates state 1988 corresponding to polymer sensor 1812 and VOC sensor 1816 and determines that an anomaly has occurred when both (a) state 1988 corresponding to VOC sensor 1816 and (b) state 1988 corresponding to polymer sensor 1812 are set to anomaly detected state 2006. Block 2214 is a decision. If, in block 2214, method 2200 determines that an anomaly has occurred, method 2200 continues with block 2216; otherwise, method 2200 returns to block 2202.

In block 2216, method 2200 sends an anomaly detected report with a module ID and timestamp to cloud detection service. In one example of block 2216, anomaly detector 1944 generates anomaly detected report 1972 and sends it to cloud detection service 1650. Method 2200 then continues with block 2202.

Detecting Marijuana Smoke and/or Tobacco Smoke in a Vehicle

Figure 23:
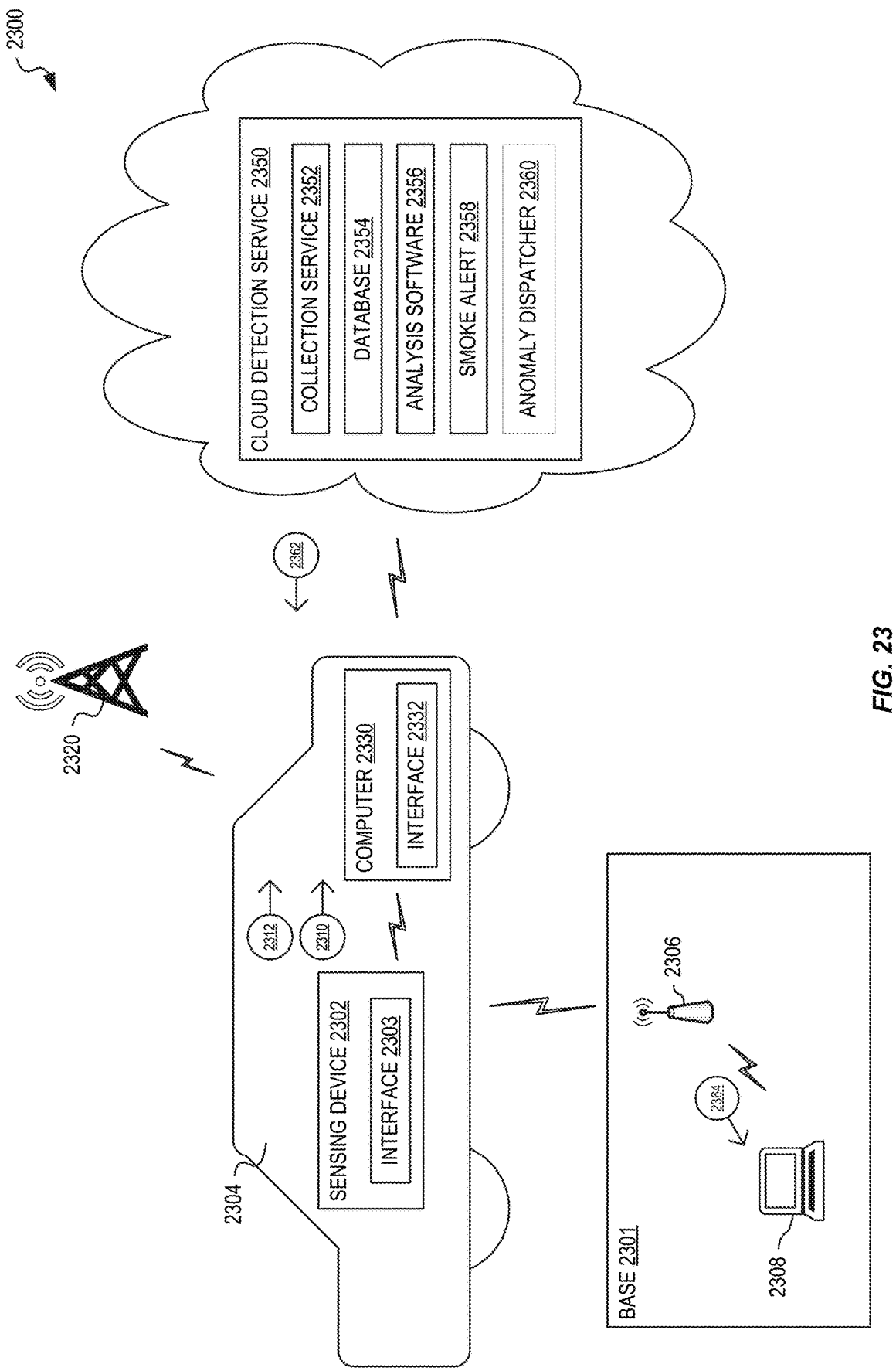
FIG. 23 shows one integrated monitoring and analysis system for detecting smoking, in embodiments.

FIG. 23 shows one example smoke detection system 2300 for detecting the use of tobacco smoke or marijuana smoke in a vehicle 2304. Hereinafter "smoke" refers to either tobacco smoke or marijuana smoke. System 2300 includes at least one sensing device 2302 and a cloud detection service 2350. Sensing device 2302 is positioned within an interior cabin space of vehicle 2304 and is operable to detect at least one of tobacco smoke and marijuana smoke using at least one polymer sensor. In the example of FIG. 23, vehicle 2304 is a car; however, vehicle 2304 may represent any type of vehicle driven by a person, such as a pick-up truck, a sport utility vehicle, an over-the-road tractor (e.g., that couples with a transport trailer), an aircraft, a bus, and so on. Sensing device 2302 is installed within vehicle 2304 and may be connected to a power source of vehicle 2304. Accordingly, sensing device 2302 includes power regulation components that converts the vehicle supplied power (e.g., 12V DC) to a suitable voltage (e.g., 3V, 5V, etc.) for use by circuitry and components of sensing device 2302. In other embodiments, sensing device 2302 includes a battery and does not require power from vehicle 2304. Sensing device 2302 is positioned within vehicle 2304 to receive airflow from around the driver and/or passengers. In certain embodiments, sensing device 2302 may include a fan that draws air from around the driver/passenger over the sensors.

Modern vehicles often include a Wi-Fi hotspot within the vehicle for use by a driver and/or passenger. As shown in FIG. 23, vehicle 2304 may therefore include a computer 2330 with at least one wireless interface 2332 that provides the Wi-Fi hot spot and includes a cellular connection to the Internet, via a cell tower 2320 for example. Computer 2330 and interface 2332 are not part of system 2300, but may be used for communication between sensing device 2302 and cloud detection service 2350. Sensing device 2302 includes an interface 2303 (e.g., a short-range wireless interface implementing one or more of Bluetooth, Zwave, ZigBee, Wi-Fi, etc.) that allows sensing device 2302 to communicate with interface 2332 of computer 2330. In situations where vehicle 2304 does not include computer 2330 and/or a Wi-Fi hot spot, interface 2303 of sensing device 2302 may include a cellular interface that allows sensing device 2302 to communicate with cloud detection service 2350 via the cell tower 2320.

Cloud detection service 2350 is similar to cloud detection service 150 of FIG. 1 and may include similar functionality. For example, cloud detection service 2350 may include a database 2354 that associates a client device 2308 (e.g., a computer, laptop, tablet, smartphone, etc.) with sensing device 2302. For example, client device 2308 may be used by an owner and/or operator of vehicle 2304. As shown in FIG. 23, vehicle 2304 and/or client device 2308 may be associated with a base 2301 that represents a base location (e.g., an owner's home, a bus depot, a rental garage, and so on) for vehicle 2304. Base 2301 may include a local wireless network 2306 communicatively coupled with the Internet. Accordingly, when vehicle 2304 is at the location of base 2301, sensing device 2302 may communicate with cloud detection service 2350 via local wireless network 2306 using one or more wireless (or wired e.g., Ethernet) protocols, including Wi-Fi, Bluetooth, Zwave, ZigBee, and so on.

When sensing device 2302 detects smoke within vehicle 2304, sensing device 2302 sends a message 2310 identifying itself (see device ID 2408, FIG. 24), indicating a time that smoke was sensed, and corresponding sensor data (e.g., raw sensor data collected for a period including the time of detection) to cloud detection service 2350. When communication with cloud detection service 2350 is unavailable, sensing device 2302 stores message 2310 within its memory, sending message 2310 when communication becomes available (e.g., when vehicle 2304 returns to base 2301 and sensing device 2302 connects with local wireless network 2306). In certain embodiments, sensing device 2302 sends an alert indicating smoke detection to client device 2308 (e.g., via computer 2330 and its Wi-Fi hot spot, via local wireless network 2306, and/or directly using Bluetooth or similar short range wireless protocols when client device 2308 is within range). In other embodiments, sensing device 2302 sends message 2310 to cloud detection service 2350, and cloud detection service 2350 sends an alert to client device 2308.

In certain embodiments, sensing device 2302 buffers raw sensor data and waits for collection service 2352 to request raw data in response to receiving message 2310 reporting the time of the anomaly. For example, collection service 2352 sends a message 2362 requesting sensor data from the identified sensing device 2302, which, in response, sends the corresponding sensor data, shown as message 2312, to cloud detection service 2350. In other embodiments, collection service 2352 may receive raw sensor data from sensing device 2302 at intervals (e.g., as blocks of data), or continuously as it is captured. Accordingly, when sensing device 2302 sends message 2310 identifying itself and indicating the time of the anomaly to cloud detection service 2350, raw sensor data corresponding to the anomaly has already been received by collection service 2352.

Analysis software 2356 of cloud detection service 2350 further analyzes the raw sensor data and generates a smoke alert 2358 when the raw sensor data indicates smoke is detected. As described in detail below, analysis software 2356 may use artificial intelligence (AI) algorithms and techniques to analyze raw sensor data captured from at least two different sensors of sensing device 2302 to determine further details of smoke alert 2358. Analysis software 2356 may implement self-learning to improve analysis and detection of air quality anomalies over time. An anomaly dispatcher 2360 of the cloud detection service 2350 identifies client device 2308 as being associated with sensing device 2302 and sends a message 2364 including smoke alert 2358 to client device 2308.

Figure 24:
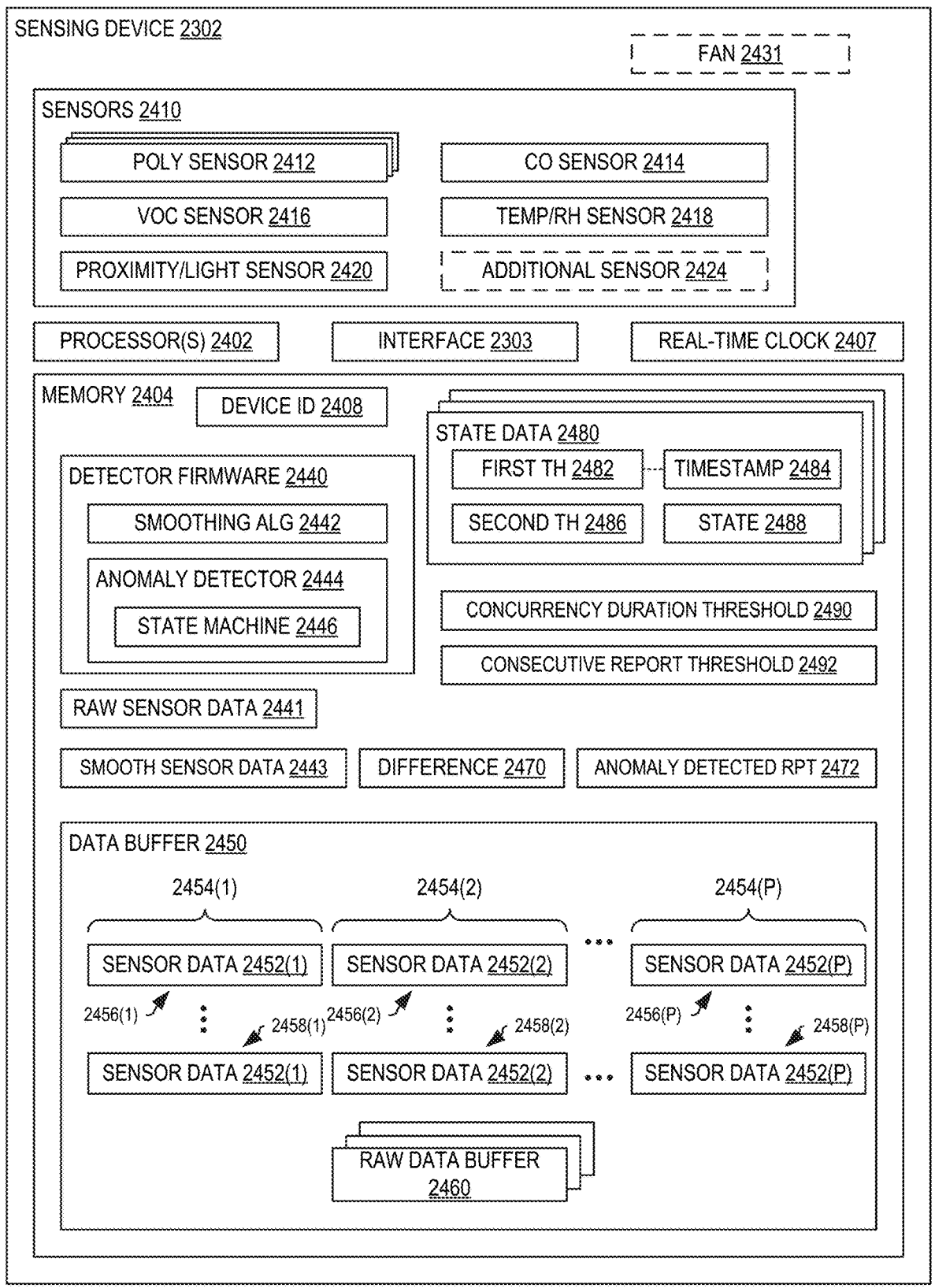
FIG. 24 is a block diagram showing the sensing device of FIG. 23 in further example detail, in embodiments.

FIG. 24 is a block diagram illustrating sensing device 2302 of FIG. 23 in further example detail. FIGS. 23 and 24 are best viewed together with the following description. Sensing device 2302 may include a plurality of sensors 2410, including at least one polymer sensor 2412 that senses a level of a targeted molecule (e.g., smoke) in the air, and a carbon monoxide (CO) sensor 2414 that senses a level of CO in the air, and one or more environmental sensors such as a volatile organic compound (VOC) sensor 2416, a temperature/relative humidity/atmospheric pressure sensor 2418, and a proximity/light sensor 2420. In certain embodiments, sensing device 2302 is configurable to include up to three different types of polymer sensors 2412, each detecting a different environmental pollutant in the ambient air such as one or more of tobacco smoke, marijuana smoke, toxic industrial chemicals, bacteria, etc. The environmental sensors may sense temperature, relative and/or absolute humidity, volatile organic chemical concentration, atmospheric pressure, and so on, and may be used to calibrate the response of the molecule specific sensors 2412, 2414. Sensing device 2302 may include one or more additional sensors 2424 without departing from the scope hereof. Sensors 2410 are positioned, within a housing of sensing device 2302 that may be vented to allow air to flow over sensors 2410. In certain embodiments, the airflow may be aided by a fan 2431.

Sensing device 2302 may include at least one processor 2402 communicatively coupled with memory 2404 storing detector firmware 2440 that includes machine-readable instructions which, when executed by processor 2402, cause processor 2402 to implement functionality of sensing device 2302 as described herein. Sensing device 2302 also includes interface 2303 for communicating with at least local wireless network 2306 and a real-time clock 2407 that maintains a current time and date. In certain embodiments, interface 2303 (and/or detector firmware 2440) may implement a Bluetooth beacon, described in further detail below. In certain embodiments, detector firmware 2440 and interface 2303 may implement a Message Queuing Telemetry Transport (MQTT) protocol, operating over the TCP/IP network, to communicate with cloud detection service 2350. The MQTT protocol enables two-way communication such that cloud detection service 2350 may initiate communication to individual sensing devices 2302 when needed (e.g., to send sensing parameter updates, Wi-Fi network updates, and so on), to prevent data loss by implementing the different levels of packet reception acknowledgment (e.g., quality of service), and to reduce the size of transmitted data as compared to the regular HTTP protocol. Detector firmware 2440 may synchronize, once and/or periodically, real-time clock 2407 to an online time service as known in the art. In other embodiments, detector firmware 2440 may implement and maintain real-time clock 2407 in memory 2404 using software. Sensing device 2302 may also implement the HTTP protocol to send and/or receive one or more of status, operation logs, updated parameters, and firmware, with cloud detection service 2350, particularly when the MQTT protocol is disabled or blocked by a client Wi-Fi network (e.g., based on firewall settings).

Memory 2404 also stores a device ID 2408 that uniquely identifies sensing device 2302 to cloud detection service 2350. For example, device ID 2408 may be included within messages sent by sensing device 2302 to cloud detection service 2350 such that cloud detection service 2350 attributes the messages and their content to the correct sensing device 2302.

Memory 2404 also includes a data buffer 2450 for storing sensor data 2452 determined from at least one of sensors 2410. In certain embodiments, data buffer 2450 may implement, for each sensor 2410, an independent cyclic buffer 2454 that stores several minutes' worth of sensor data 2452. In one embodiment, data buffer 2450 stores sensor data 2452 for a period of five-minutes (e.g., three hundred sensor data 2452 entries for each sensor when sensor data 2452 is determined at a rate of one per second). However, in certain other embodiments, data buffer 2450 may be larger and store more than five-minutes' worth of sensor data 2452. In the example of FIG. 24, data buffer 2450 is shown with P (an integer greater than or equal to 3) cyclic buffers 2454(1)-(P), each storing sensor data for a different one of sensors 2410 and each having a head 2456 and a tail 2458. Data buffer 2450 may also store, for each of sensors 2410, a raw data buffer 2460 that stores raw sensor data read from each of sensors 2410. Each raw data buffer 2460 is implemented as a cyclic buffer that stores at least forty-five-minutes' worth of raw sensor data 2441 read from one of sensors 2410. Accordingly, sensing device 2302 also maintains a history of raw sensor data captured over the last forty-five minutes. In embodiments where connectivity is not readily available to sensing device 2302, raw data buffer 2460 may be larger and implemented in non-volatile memory such that sensing device 2302 may store raw sensor data 2441 until communication is available, wherein it may be uploaded to cloud detection service.

Detector firmware 2440 includes a smoothing algorithm 2442 and an anomaly detector 2444. Detector firmware 2440 reads raw sensor data (shown as raw sensor data 2441 in memory 2404) from at least one of sensors 2410 at intervals (e.g., once per second), stores the raw sensor data 2441 in the corresponding raw data buffer 2460, invokes smoothing algorithm 2442 to process the raw data and determine smoothed sensor data 2443, and stores smoothed sensor data 2443 at head 2456 of the corresponding cyclic buffer 2454 of data buffer 2450, where it is shown as sensor data 2452. For example, detector firmware 2440 may use an internal timer of processor 2402 to determine an interval of one second between reading of raw sensor data from polymer sensor 2412. In certain embodiments, smoothing algorithm 2442 is an exponential smoothing function that is parametrized to dampen fast deviations in raw data read from sensors 2410. Data buffer 2450 thereby maintains, in combination with smoothing algorithm 2442, a baseline for each monitored sensor that may change (e.g., drift slowly) over time. An anomaly in air quality is identified when sensed conditions change faster than expected. That is, sensed conditions of clean air are expected to change gradually (e.g., change by small amounts over long periods). Accordingly, the corresponding baseline may also change gradually over time. For example, each cyclic buffer 2454 stores the smoothed sensor data 2443 for at least five minutes, where sensor data 2452 at tail 2458 of cyclic buffer 2454 is smoothed sensor data 2443 that was calculated five minutes ago. Cyclic buffers 2454 may be configured to store sensor data 2452 for other periods without departing from the scope hereof. In certain embodiments, the period of cyclic buffers 2454 is configurable by cloud detection service 2350.

To detect anomalies in the air quality, detector firmware 2440 invokes anomaly detector 2444 to evaluate smoothed sensor data 2443 for one or more of sensors 2410 against a corresponding baseline for that sensor. In the example of FIG. 24, where sensing device 2302 includes polymer sensor 2412 and CO sensor 2414, anomaly detector 2444 may be configured to monitor sensor data 2452 for only these sensors. For each monitored sensor, anomaly detector 2444 compares the most recently determined sensor data 2452 (e.g., after the raw data is processed by smoothing algorithm 2442) with a baseline value read from tail 2458 of the corresponding cyclic buffer 2454 of data buffer 2450 for that sensor to determine a difference 2470. For example, where cyclic buffer 2454(1) stores sensor data 2452(1) corresponding to polymer sensor 2412, anomaly detector 2444 may determine difference 2470 by subtracting sensor data 2452(1) at tail 2458(1) of cyclic buffer 2454(1) from sensor data 2452(1) at head 2456(1) of cyclic buffer 2454(1). That is, difference 2470 represents change from a smoothed sensed value that occurred five minutes ago and a current smoothed sensed value. Accordingly, difference 2470 represents changes in sensed air quality that has occurred within the last five-minute period.

Certain aspects of the present embodiments include the realization that a false positive may occur when a simple threshold value is used to trigger air quality anomalies, since one or more sample values greater than a trigger threshold may occasionally occur without a significant air quality anomaly. Advantageously, the present embodiments solve this problem by including a state machine 2446 in anomaly detector 2444 that detects when a slope of consecutive differences in sensor data 2452 for each monitored sensor indicates a continued change (increase or decrease) in sensor data 2452 and thereby more strongly indicates when to send an anomaly report to cloud detection service 2350 as compared to evaluating a single difference. Particularly, state machine 2446 confirms when a change indicated by a monitored sensor is consistent. Advantageously, state machine 2446 reduces the number of air quality anomaly false positives indicated by sensing device 2302.

Figure 25:
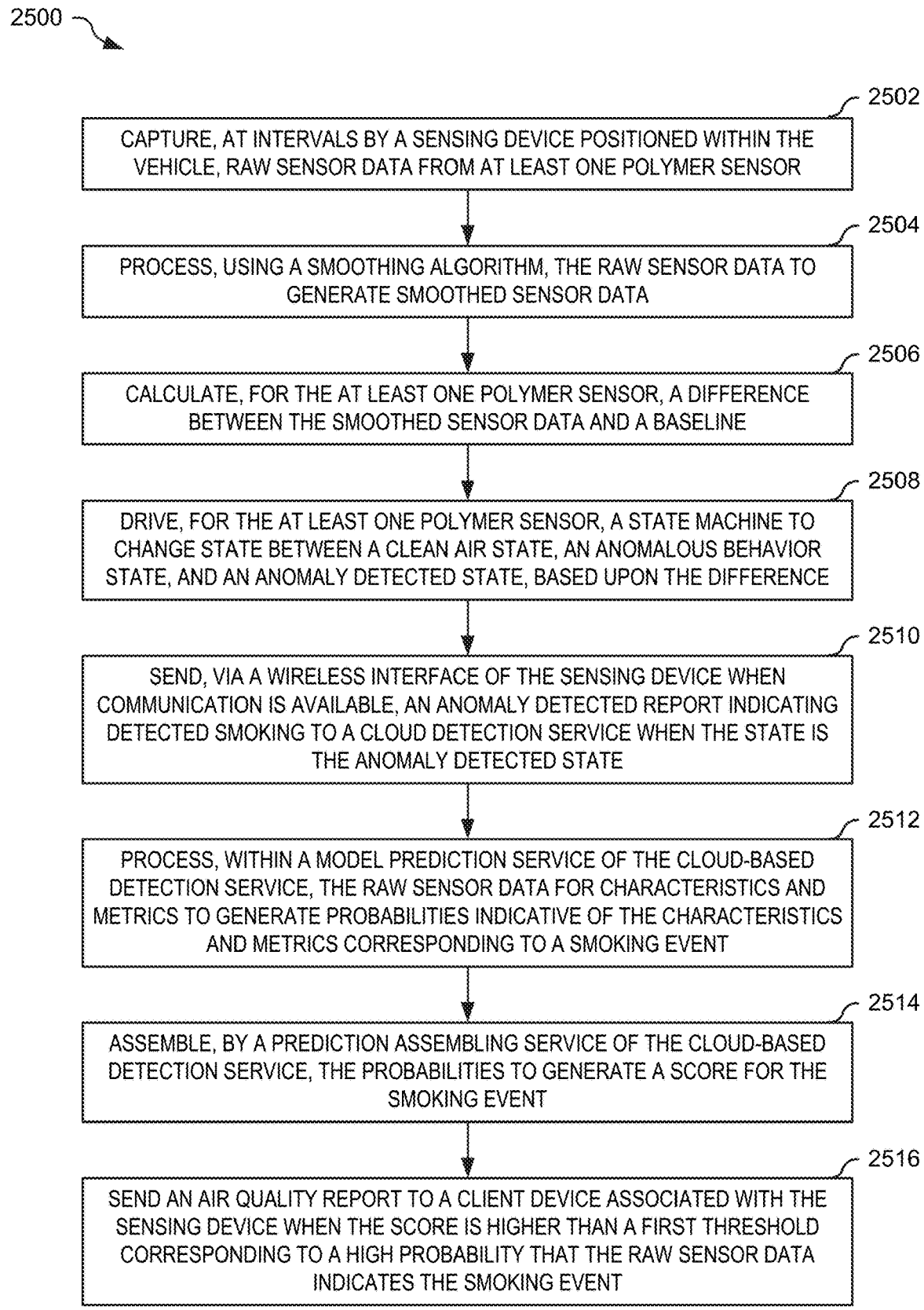
FIG. 25 is a flowchart illustrating one example method for detecting smoking in a vehicle, in embodiments.

FIG. 25 is a flowchart illustrating one example method 2500 for detecting smoking within a vehicle. In some implementations, one or more blocks of method 2500 may be performed by a sensing device (e.g., sensing device 2302). In some implementations, one or more blocks of method 2500 may be performed by another device or a group of devices separate from or including the sensing device. Additionally, or alternatively, one or more blocks of method 2500 may be performed by one or more components of sensing device 2302, such as processor 2402, memory 2404, and/or interface 2303.

As shown in FIG. 25, method 2500 may include capturing, at intervals by a sensing device positioned within the vehicle, raw sensor data from at least one polymer sensor (block 2502). In one example of block 2502, sensing device 2302, positioned within vehicle 2304, may capture raw sensor data 2441 from polymer sensor 2412, as described above.

As further shown in FIG. 25, method 2500 may include processing, using a smoothing algorithm, the raw sensor data to generate smoothed sensor data (block 2504). In one example of block 2504, sensing device 2302 processes, using smoothing algorithm 2442, raw sensor data 2441 to generate smoothed sensor data 2443, as described above.

As further shown in FIG. 25, method 2500 may include calculating, for the at least one polymer sensor, a difference between the smoothed sensor data and a baseline (block 2506). In one example of block 2506, sensing device 2302 calculates, for the at least one polymer sensor 2412, difference 2470 between smoothed sensor data 2443 and the baseline sensor data 2452(1) at tail 2458(1) of data buffer 2450, as described above.

As further shown in FIG. 25, method 2500 may include driving, for the at least one polymer sensor, a state machine to change state between a clean air state, an anomalous behavior state, and an anomaly detected state, based upon the difference (block 2508). In one example of block 2508, sensing device 2302 drives, for the at least one polymer sensor 2412, state machine 2446 to change state between a clean air state 302, an anomalous behavior state 304, and an anomaly detected state 306, based upon difference 2470, as described above.

As further shown in FIG. 25, method 2500 may include sending, via a wireless interface of the sensing device when communication is available, an anomaly detected report indicating detected smoking to a cloud detection service when the state is the anomaly detected state (block 2510). In one example of block 2510, sensing device 2302 sends, via wireless interface 2303 when communication is available, an anomaly detected report 2472 indicating detected smoking to cloud detection service 2350 when the state 2488 is anomaly detected state 306, as described above.

As further shown in FIG. 25, method 2500 may include processing, within a model prediction service of the cloud detection service, the raw sensor data for characteristics and metrics to generate probabilities indicative of the characteristics and metrics corresponding to a smoking event (block 2512). In one example of block 2512, model prediction service 606 of cloud detection service 2350 processes raw sensor data from raw data buffer 2460 for characteristics and metrics to generate probabilities indicative of the characteristics and metrics corresponding to a smoking event, as described above.

As further shown in FIG. 25, method 2500 may include assembling the probabilities to generate a score for the smoking event (block 2514). In one example of block 2514, cloud detection service 2350 assembles the probabilities to generate a score for the smoking event, as described above.

As further shown in FIG. 25, method 2500 may include sending an air quality report to a client device associated with the sensing device when the score is higher than a first threshold corresponding to a high probability that the raw sensor data indicates the smoking event (block 2516). In one example of block 2516, cloud detection service 2350 sends smoke alert 2358 to client device 2308 associated with sensing device 2302 when the score is higher than a first threshold corresponding to a high probability that the raw sensor data indicates the smoking event, as described above.

Method 2500 may include additional implementations, such as any single implementation or any combination of implementations described below and/or in connection with one or more other methods described elsewhere herein.

Although FIG. 25 shows example blocks of method 2500, in some implementations, method 2500 may include additional blocks, fewer blocks, different blocks, or differently arranged blocks than those depicted in FIG. 25. Additionally, or alternatively, two or more of the blocks of method 2500 may be performed in parallel. Service Quality Control Another aspect of the present embodiments includes the realization that hotels, and similar establishments, typically use a paper chart (e.g., a tick list) to indicate when rooms are serviced. Coordination and management of these paper charts is difficult and error prone. A service tracking system solves this problem by including, within each room requiring servicing, a short range wireless beacon (e.g., a Bluetooth beacon) that is detectable by an application running on a client device of service personnel when in the room. Advantageously, the system automatically logs and reports presence of servicing personnel within the room to a server that determines when a room requiring servicing as not been serviced. The system may generate reports and/or alerts to indicate rooms that have not been serviced within a defined period.

Figure 26:
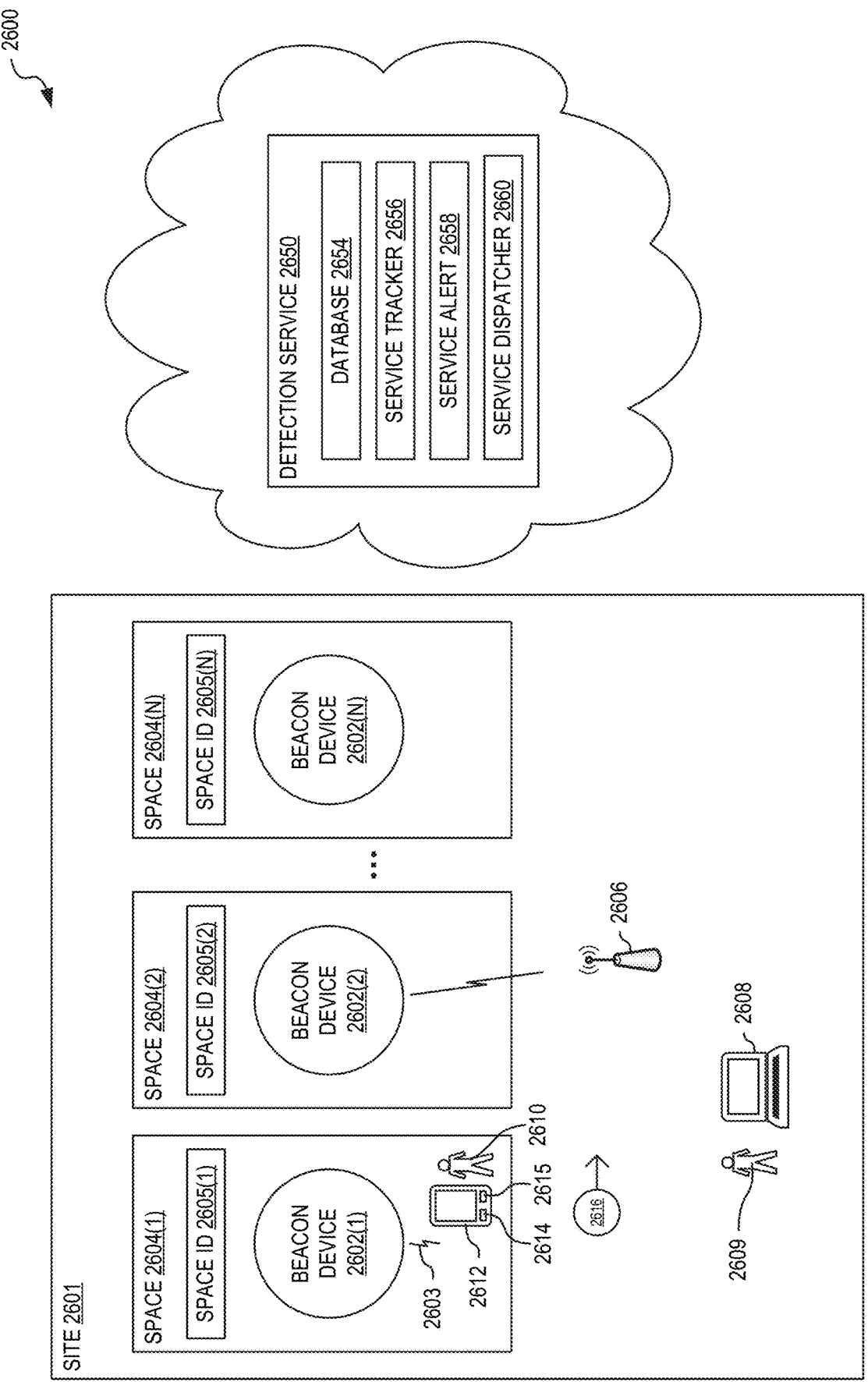
FIG. 26 is a schematic diagram illustrating one example service quality control system, in embodiments.

FIG. 26 is a schematic diagram illustrating one example service quality control system 2600. The following examples use servicing of hotel rooms; however, the servicing may be of any space at any site where tracking provides an improvement in service quality. For example, system 2600 may track specific servicing of and/or response to reported problems at a manufacturing site, or may track scheduled servicing of equipment throughout the manufacturing site. System 2600 includes a plurality of beacon devices 2602 that are each positioned within a different space 2604(1)-(N) (e.g., hotel room) at a site 2601 (e.g., hotel), and a cloud detection service 2650. Each space 2604 may have an associate space ID 2605(1)-(N) (e.g., a room number, address, etc.) Beacon device 2602 may represent a bespoke stand-alone device or may represent one of sensing device 102, FIG. 1, sensor module 1602 and/or control module 1603 of FIG. 16, and sensing device 2302 of FIG. 23. That is, functionality of beacon device 2602 may be incorporated into other devices, without departing from the scope hereof. This advantageously uses the already installed sensing devices 102 and/or sensor module 1602 to implement the described service quality control.

Figure 27:
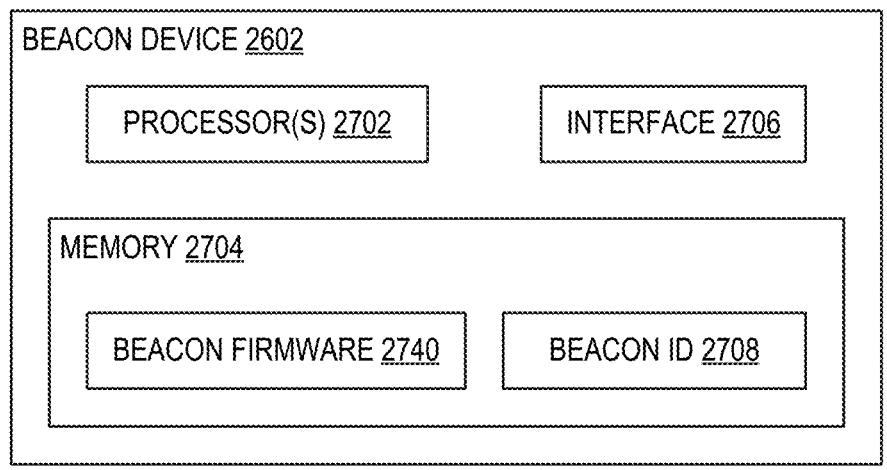
FIG. 27 is a block diagram illustrating the beacon device of FIG. 26 in further example detail, in embodiments.
Figure 28:
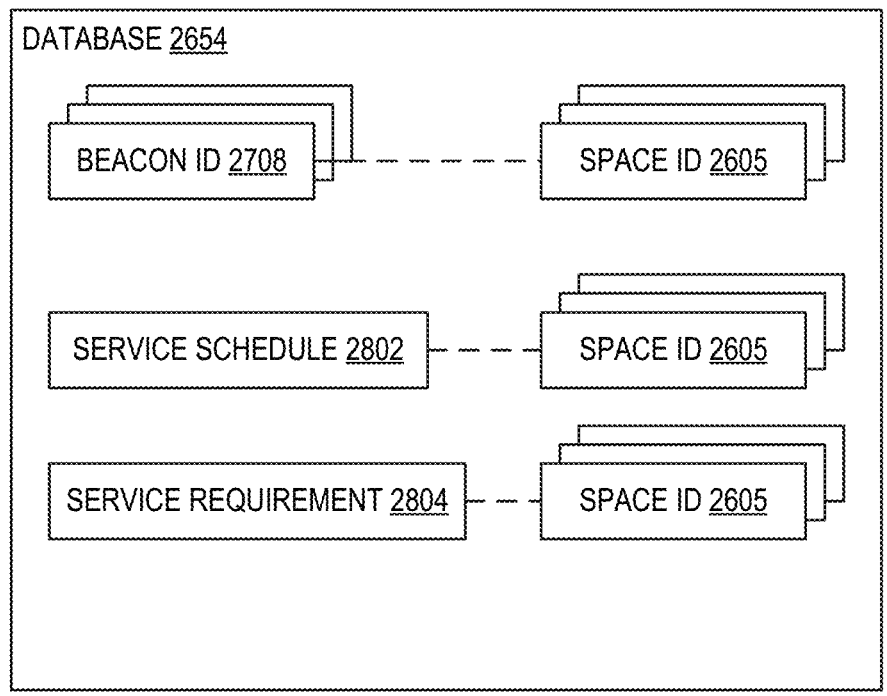
FIG. 28 is a block diagram illustrating the database of the service quality control system of FIG. 26 in further detail, in embodiments.

FIG. 27 is a block diagram illustrating beacon device 2602 in further example detail. FIG. 28 is a block diagram illustrating database 2654 of service quality control system 2600 in further example detail. FIGS. 26, 27 and 28 are best viewed together with the following description. Beacon device 2602 includes a beacon ID 2708 that uniquely identifies beacon device 2602 and an interface 2706 for generating a short-range wireless beacon 2603 (e.g., a Bluetooth beacon) that includes beacon ID 2708. For example, beacon ID 2708 is encoded within beacon 2603 such that beacon 2603 is also uniquely identifiable. Servicing personnel 2610 carry a mobile device 2612 (e.g., a smartphone, a wearable device such as a smart watch, or other such device) executing an application 2614 (e.g., a downloadable app or installed firmware) that may receive beacon 2603 when servicing personnel 2610 enters space 2604.

Cloud detection service 2650 includes a database 2654 that associates each beacon ID 2708 with space ID 2605 based on the installation of beacon device 2602 within the corresponding space 2604. For example, database 2654 may associate beacon ID 2708 of beacon device 2602(1) with a corresponding space ID 2605(1) of space 2604(1). Database 2654 may also store other information relevant to each space 2604, such as account details (e.g., name, address, users, etc.). Database 2654 may also store a service schedule 2802 defining when each space ID 2605 should be serviced (e.g., a requested or scheduled servicing of spaces 2604). In one example, service schedule 2802 defines that spaces 2604 (1)-(N) should be serviced each day between l.OAM and noon. Database 2654 may also include a service requirement 2804 that defines a check procedure and requirement for each associated space 2604. For example, service requirement 2804 is associated with all spaces 2604 when the check procedure and requirement is account-wide, whereas service requirement 2804 is associated with some spaces 2604 where the check procedure and requirement is location specific.

Database 2654 also associates a client device 2608 (e.g., a computer, laptop, tablet, smartphone, etc.) with site 2601, and/or spaces 2604, and/or beacon devices 2602 located at that site. For example, client device 2608 may be used by a supervisor 2609 (e.g., an owner, manager, and/or authorized person) of site 2601 and/or of servicing personnel 2610. Site 2601 may include a local wireless network 2606 (e.g., Wi-Fi) communicatively coupled with the Internet.

Beacon 2603 includes the corresponding beacon ID 2708 that is received and decoded by application 2614 when mobile device 2612 is within space 2604. In certain embodiments, application 2614 may also use a received signal strength indication (RSSI) to verify its proximity to beacon device 2602. In other embodiments, beacon device 2602 causes beacon 2603 to have a transmitted signal strength such that direct proximity (e.g., being located within the corresponding space 2604 and near beacon device 2302) is required for mobile device 2612 to receive beacon 2603. This reduces the likelihood of false positive detection of beacon 2603.

Mobile device 2612 includes a mobile device ID 2615 that is unique to mobile device 2612. When application 2614 receives beacon 2603, application 2614 may send a message 2616 including mobile device ID 2615 and beacon ID 2708 decoded from beacon 2603 to detection service 2650, via local wireless network 2606 for example. Message 2616 may also include a time stamp indicating the time that mobile device 2612 detected and decoded beacon 2603. In response to message 2616, a service tracker 2656 of detection service 2650 may update database 2654 to indicate proximity of mobile device 2612 to beacon device 2602 and thereby imply that space 2604 has been visited by service personnel 2610.

In certain embodiments, application 2614 may send a message to detection service 2650 to indicate when beacon 2603 is no longer received by mobile device 2612, whereby service tracker 2656 may update database 2654 to indicate a duration of the visit to space 2604 by servicing personnel 2610. In certain embodiments, service tracker 2656 sends service requirements 2804 corresponding to the space ID 2605 received in message 2616 back to application 2614, whereby application 2614 may prompt service personnel 2610, via mobile device 2612 to inspect space 2604 and indicate that service requirements and inspection have been completed. Application 2614 then sends another message with the inspection results to detection service 2650, and service tracker 2656 updates database 2654 accordingly.

Detection service 2650 includes an interactive web interface (e.g., servicing dashboard) that allows supervisor 2609, using client device 2608 for example, to define one or more of service schedule 2802 and service requirement 2804 for spaces 2604. For example, knowing that guests are leaving space 2604(1) by noon, supervisor 2609 updates service schedule 2802 within database 2654 to indicate space 2604 (1) is to be serviced between noon and 3 PM. When service tracker 2656 determines that space 2604(1) was not serviced (e.g., database 2654 does not indicate service personnel 2610 visited space 2604(1)) between noon and 3 PM, service tracker 2666 generates and sends a service alert 2658 (e.g., a notification), indicating that space 2604(1) has not been serviced, to client device 2608. In certain embodiments, service tracker 2656 generates and sends service alert 2658 to mobile device 2612 to prompt servicing personnel 2610 to service space 2604. Advantageously, supervisor 2609 is made aware of the anomaly and may direct servicing personnel 2610 to space 2604(1). Accordingly, system 2600 provides an improvement in quality and reliability of servicing of spaces 2604. In certain embodiments, detection service 2650 also includes a service dispatcher 2660 that, based on service schedule 2802 and received messages 2616 (or lack thereof), automatically sends servicing requests directly to application 2614 running on mobile device 2612 to request servicing of spaces 2604.

As shown in FIG. 27, beacon device 2602 may include at least one processor 2702 communicatively coupled with memory 2704 storing beacon firmware 2740 that includes machine-readable instructions that, when executed by processor 2702, cause processor 2702 to implement functionality of beacon device 2602 as described herein. Beacon firmware 2740 controls interface 2706 that implements beacon 2603.

Figure 29:
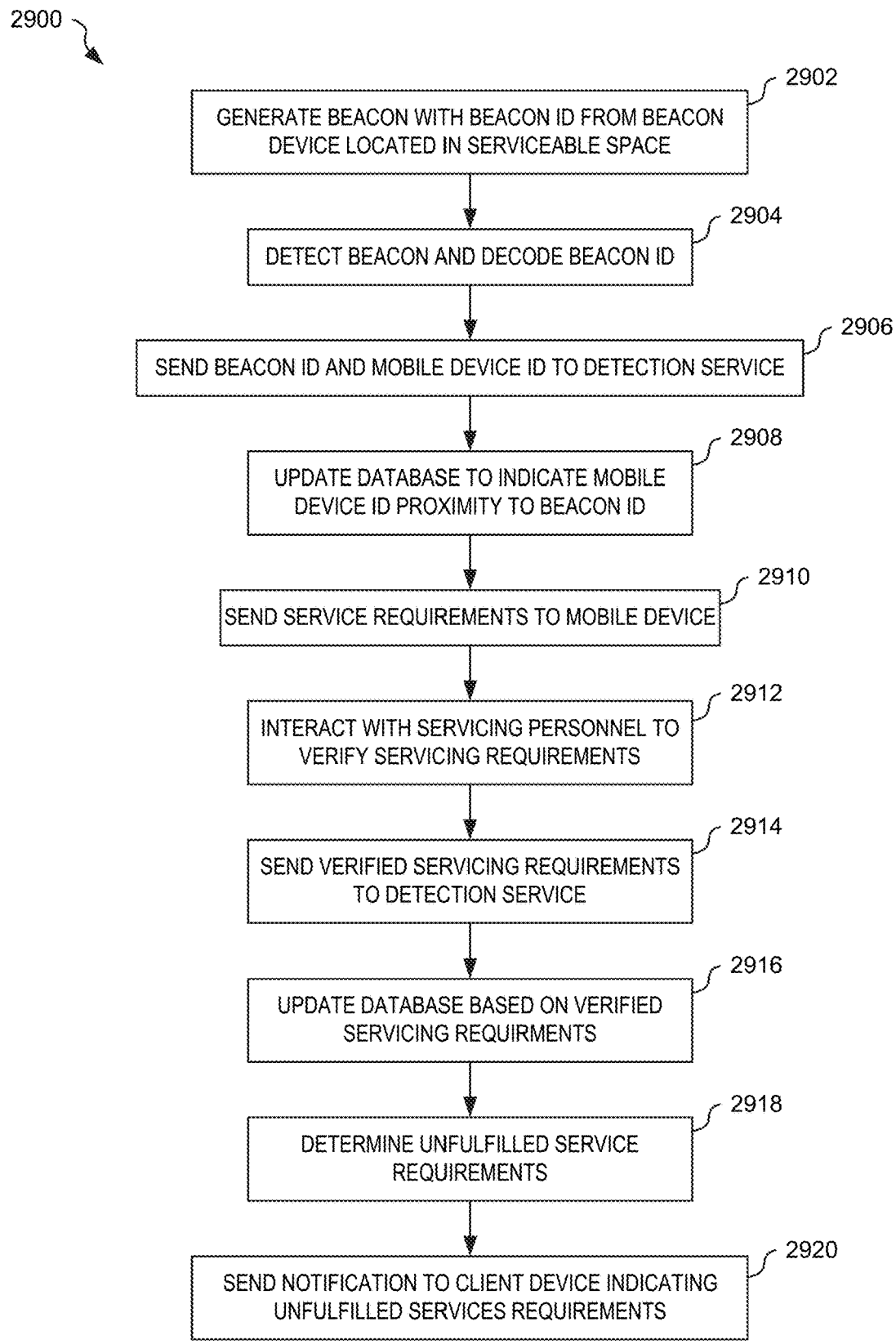
FIG. 29 is a flowchart illustrating one example method for service quality control, in embodiments.

FIG. 29 is a flowchart illustrating one example method 2900 for service quality control. Block 2902 is implemented within beacon device 2602 of FIGS. 26 and 27, for example. Blocks 2904, 2906, 2912, and 2914 are implemented by application 2614 running on mobile device 2612, for example. Blocks 2908, 2910, 2916, 2918, and 2920 are implemented by detection service 2650, for example. One or more blocks of method 2900 may be performed by other devices or a group of devices separate from or including beacon device 2602, application 2614, and detection service 2650.

In block 2902, method 2900 generates a wireless beacon with a beacon ID from a beacon device located within a serviceable space. In one example of block 2902, beacon firmware 2740 causes processor 2702 of beacon device 2602, located in space 2604, to control interface 2706 to generate beacon 2603 including beacon ID 2708. In block 2904, method 2900 detects the beacon and decodes the beacon ID. In one example of block 2904, application 2614 controls mobile device 2612 to receive beacon 2603 and decode beacon ID 2708 therefrom. In block 2906, method 2900 sends the beacon ID and a mobile device ID to the detection service. In one example of block 2906, application 2614 causes mobile device 2612 to send message 2616, including beacon ID 2708 and mobile device ID 2615, to detection service 2650. In block 2908, method 2900 updates its database to indicate mobile device ID proximity to beacon ID. In one example of block 2908, service tracker 2656 updates database 2654 to indicate space 2604 visited by mobile device 2612.

In block 2910, method 2900 sends service requirements to the mobile device. In one example of block 2910, service tracker 2656 sends service requirements 2804 corresponding to space ID 2605 to mobile device 2612. In block 2912, method 2900 interacts with servicing personnel to verify servicing requirements. In one example of block 2912, application 2614 interacts, using mobile device 2612, with service personnel 2610 to verify servicing requirements 2804 were performed. In block 2914, method 2900 sends verified servicing requirements to the detection service. In one example of block 2914, application 2614 sends a message with the servicing verification results to detection service 2650. In block 2916, method 2900 updates the database based on the verified servicing requirements. In one example of block 2916, service tracker 2656 updates database 2654 based on the verified service requirements received from mobile device 2612. In block 2918, method 2900 determines unfulfilled service requirements. In one example of block 2918, service tracker 2656 processes database 2654 to determine unfulfilled service requirements based on at least service schedule 2802, service requirements 2804, and received indications of verified services. In block 2920, method 2900 sends a notification to the client device indicating unfulfilled service requirements. In one example of block 2920, service tracker 2656 sends a notification to client device 2608 indicating that space 2604(2) was not serviced as scheduled.

Method 2900 may include additional blocks, fewer blocks, different blocks, or differently arranged blocks than those depicted in FIG. 29. Additionally, or alternatively, two or more of the blocks of method 2900 may be performed in parallel.

Combination of Features

Features described above as well as those claimed below may be combined in various ways without departing from the scope hereof. For example, it will be appreciated that aspects of one sensing device/sensing material described herein may incorporate or swap features of another sensing device/material described herein. The following examples illustrate possible, non-limiting combinations of embodiments described above. It should be clear that many other changes and modifications may be made to the methods and apparatus herein without departing from the spirit and scope of this invention:

(A) A method generates an air quality event alert for a monitored space having a sensing device. The method includes: receiving, within a cloud detection service and from the sensing device, an anomaly detected report including a timestamp for an air quality anomaly detected at the monitored space; retrieving raw sensor data captured by the sensing device using a plurality of sensors during a period including the timestamp; extracting characteristics and metrics from the raw sensor data for each of the plurality of sensors; processing the characteristics and metrics through a model prediction service to generate probabilities indicative of the characteristics and metrics corresponding to profiles of air quality events; assembling the probabilities to generate a score for the air quality anomaly corresponding to an important air quality event; and sending an air quality report when the score is higher than a first threshold corresponding to significant air quality events.

(B) The method denoted as (A) further including dismissing the air quality anomaly when the score is lower than a second threshold corresponding to insignificant air quality events.

(C) Either of the methods denoted as (A) and (B) further including marking the air quality anomaly for later analysis when the score is greater than the second threshold and less than a third threshold lower than the first threshold.

(D) Any of the methods denoted as (A)-(C) further including generating the air quality report for manual review when the score is less than the first threshold and greater than the third threshold.

(E) A method for detecting an air quality anomaly at a monitored space, including: capturing, at intervals in a sensing device located at the monitored space, raw sensor data from at least one environmental sensor, at least one carbon monoxide (CO) sensor, and at least one polymer sensor; processing, using a smoothing algorithm, the raw sensor data to generate smoothed sensor data; calculating, for at least the CO sensor and the at least one polymer sensor, a difference between the smoothed sensor data and a baseline; driving, for at least the CO sensor and the at least one polymer sensor, a state machine to change state between a clean air state, an anomalous behavior state, and an anomaly detected state, based upon the difference; and sending an anomaly detected report, indicating the air quality anomaly, to a cloud detection service when the state is the anomaly detected state.

(F) In the method denoted as (E), the smoothing algorithm including an exponential smoothing algorithm.

(G) In either of the methods denoted as (E) or (F), the baseline including smoothed sensor data calculated five-minutes earlier.

(H) Any of the methods denoted as (E)-(G) further including storing the raw sensor data in a data buffer for at least forty-five minutes.

(I) Any of the methods denoted as (E)-(H) further including sending the raw sensor data from the data buffer to the cloud detection service in response to a request for the raw sensor data from the cloud detection service.

(J) A system for monitoring air quality of a monitored space, including: at least one sensing device, located at the monitored space, the at least one sensing device having: at least one environmental sensor positioned to sense a characteristic of air within the monitored space; at least one carbon monoxide (CO) sensor positioned to sense a level of CO in the air; at least one polymer sensor positioned to sense a level of a targeted molecule in the air; an interface for communicating with a local network; a processor communicatively coupled with a memory; and detector firmware stored in the memory and having machine-readable instructions that, when executed by the processor, control the processor to: capture, at intervals, raw sensor data from the at least one environmental sensor, the at least one CO sensor, and the at least one polymer sensor; process, using a smoothing algorithm, the raw sensor data to generate smoothed sensor data; calculate, for at least the CO sensor and the at least one polymer sensor, a difference between the smoothed sensor data and a baseline; drive, for at least the CO sensor and the at least one polymer sensor, a state machine to change state between a clean air state, an anomalous behavior state, and an anomaly detected state, based upon the difference; and send, via the interface, an anomaly detected report, indicating an air quality anomaly, to a cloud detection service when the state is the anomaly detected state; and the cloud detection service including: a collection service for receiving the anomaly detected report and for receiving the raw sensor data from the at least one sensing device; a model prediction service for processing characteristics and metrics of the raw sensor data to generate probabilities indicative of the characteristics and metrics corresponding to profiles of air quality events; a prediction assembling service for assembling the probabilities to generate a score for the air quality anomaly; and sending an air quality report when the score is higher than a first threshold, the first threshold defining a value corresponding to a high probability that the raw sensor data indicates a significant air quality event.

(K) In the system denoted as (J), the at least one environmental sensor being selected from the group including a temperature sensor, a humidity sensor, an atmospheric pressure sensor, a volatile organic compound sensor.

(L) In either of the systems denoted as (J) or (K), the at least one polymer sensor targeting molecules of one or more of tobacco smoke, marijuana smoke, vaping, toxins, small molecules, bacteria, and viruses.

(M) In any of the systems denoted as (J)-(L), the detector firmware further including machine-readable instructions that, when executed by the processor, control the processor to store, within the memory, the smoothed sensor data for at least five-minutes to form the baseline.

(N) In any of the systems denoted as (J)-(M), the model prediction service including machine learning software that examines the raw sensor data and determines whether the air quality anomaly indicates an exposure event.

(O) In any of the systems denoted as (J)-(N), the air quality report being sent as one of push notification, an email, and a text message, to a client device associated with the at least one sensing device.

(P) A computer-readable media storing machine-readable instructions that, when executed by a computer, perform steps for detecting an air quality anomaly at a monitored space, including: instructions for capturing, at intervals, raw sensor data from at least one environmental sensor, at least one carbon monoxide (CO) sensor, and at least one polymer sensor; instructions for processing, using a smoothing algorithm, the raw sensor data to generate smoothed sensor data; instructions for calculating, for at least the CO sensor and the at least one polymer sensor, a difference between the smoothed sensor data and a baseline; instructions for driving, for at least the CO sensor and the at least one polymer sensor, a state machine to change state between a clean air state, an anomalous behavior state, and an anomaly detected state, based upon the difference; and instructions for sending an anomaly detected report, indicating the air quality anomaly, to a cloud detection service when the state is the anomaly detected state.

(Q) The computer-readable media denoted as (P) further including instructions for exponentially smoothing the raw sensor data.

(R) Either of the computer-readable media denoted as (P) or (Q), further including instructions for storing the smoothed sensor data for five-minutes to form the baseline.

(S) Any of the computer-readable media denoted as (P)-(R), further including instructions for storing the raw sensor data in a data buffer for at least forty-five minutes.

(T) Any of the computer-readable media denoted as (P)-(S), further including instructions for sending the raw sensor data from the data buffer to the cloud detection service in response to a request for the raw sensor data from the cloud detection service.

(U) A method for automatically detecting when a sensor requires replacement, including: receiving, within a cloud detection service and from a sensing device, raw sensor data from the sensor; processing, using a long-term exponential smoothing algorithm, the raw sensor data to generate baseline values; determining that the sensor has failed when the baseline values is not within an operational baseline range of the sensor; and notifying a customer support team of the failed sensor.

(V) The method denotes as (U) further including: detecting a rapid change in the baseline values; detecting gaps in the raw sensor data received from the sensing device; and determining that the sensor has been replaced based on the rapid change in the baseline values and the gap in the raw sensor data corresponding to the rapid change.

(W) A method for detecting vaping in a space where vaping is prohibited, including: capturing, at intervals by a senor module positioned within an air extraction duction of the space, raw sensor data from at least one polymer sensor; processing, using a smoothing algorithm, the raw sensor data to generate smoothed sensor data; calculating, for the at least one polymer sensor, a difference between the smoothed sensor data and a baseline; sending, via the interface, an alert and raw sensor data to a control module when the difference is greater than a threshold; processing, within the control module, the raw sensor data to detect the vaping; and sending a vaping report indicative of the detected vaping.

(X) In the method denoted as (W), the step of sending including sending the vaping report to a client device associated with the space.

(Y) In either of the methods denoted as (W) or (X), the step of sending including sending the vaping report to a cloud detection service.

(Z) A system for detecting vaping in a space where vaping is prohibited, including: a sensor module having: a housing sized and shaped to fit within an air extraction duct fluidly coupled with the space; at least one polymer sensor positioned within the housing to receive air flowing through the air extraction duct and operable to sense a level of a targeted molecule associated with vaping; a first short range wireless interface; a processor communicatively coupled with a memory; and detector firmware stored in the memory and having machine-readable instructions that, when executed by the processor, control the processor to: capture, at intervals, raw sensor data from the at least one polymer sensor; and send, via the first short range wireless interface, a first message including raw sensor data to a control module; the control module having: a second short range wireless interface; a network interface; a second processor communicatively coupled with a second memory; and controller firmware stored in the second memory and having machine-readable instructions that, when executed by the processor, cause the second processor to: receive the first message via the second short range wireless interface; process, using a smoothing algorithm, the raw sensor data to generate smoothed sensor data; calculate, for the at least one polymer sensor, a difference between the smoothed sensor data and a second baseline; drive, based upon the difference for the at least one polymer sensor, a state machine to change state between a clean air state, an anomalous behavior state, and an anomaly detected state; and send an anomaly detected report, indicating vaping is detected when the state is the anomaly detected state.

(AA) In the system denoted as (Z), the sensor module further including one or more of a temperature sensor, a humidity sensor, and volatile organic compound (VOC) sensor, positioned within the housing to receive the air flowing through the air extraction duct, the raw sensor data including sensor data from the one or more of the temperature sensor, the humidity sensor, and the VOC sensor.

(AB) In either of the systems denoted as (Z) or (AA), the first short range wireless interface and the second short range wireless interface implementing a Bluetooth protocol.

(AC) In any of the systems denoted as (A)-(AB), the controller firmware operable to communicate with more than one sensor module.

(AD) Any of the systems denoted as (A)-(AC) further including a cloud detection service, the controller firmware comprising further machine-readable instructions that when executed by the second processor cause the second processor to transmit the anomaly detected report and the raw sensor data corresponding to the detected vaping to the cloud detection service.

(AE) In any of the systems denoted as (Z)-(AD), the cloud detection service implementing at least one algorithm to analyzes the raw sensor data to determine if vaping has occurred.

(AF) In any of the systems denoted as (Z)-(AE), the anomaly detected report being sent to a client device associated with the space as one or more of an email, a push notification, and a text message.

(AG) In any of the systems denoted as (Z)-(AF), the controller firmware including further machine-readable instructions that when executed by the second processor cause the second processor to store, within the anomaly detected report, a time of the detected vaping.

(AH) A method for detecting smoking in a vehicle where smoking is prohibited, including: capturing, at intervals by a sensing device positioned within the vehicle, raw sensor data from at least one polymer sensor; processing, using a smoothing algorithm, the raw sensor data to generate smoothed sensor data; calculating, for the at least one polymer sensor, a difference between the smoothed sensor data and a baseline; driving, for the at least one polymer sensor, a state machine to change state between a clean air state, an anomalous behavior state, and an anomaly detected state, based upon the difference; and sending, via a wireless interface of the sensing device, an anomaly detected report indicating the detected smoking.

(AI) The method denoted as (AH) further including: sending raw sensor data corresponding to the detected smoking to a cloud detection service when the state is the anomaly detected state; processing, within a model prediction service of the cloud detection service, the raw sensor data for characteristics and metrics to generate probabilities indicative of the characteristics and metrics corresponding to a smoking event; assembling, by a prediction assembling service of the cloud detection service, the probabilities to generate a score for the smoking event; and sending an air quality report to a client device associated with the sensing device when the score is higher than a first threshold corresponding to a high probability that the raw sensor data indicates the smoking event.

(AJ) In either of the methods denoted as (AH) or (AI), the step of sending the anomaly detected report including sending the anomaly detected report to a client device associated with the vehicle.

(AK) In any of the methods denoted as (AH)-(AJ), the step of sending the anomaly detected report including sending the anomaly detected report to a computer of the vehicle.

(AL) A system to detect the occurrence of smoking in a vehicle where smoking is prohibited, including: a sensor module having: a housing sized and shaped to fit within a cabin of the vehicle; at least one polymer sensor positioned within the housing and operable to sense a level of a targeted molecule associated with smoking in air within the cabin; a wireless interface; a processor communicatively coupled with a memory; and detector firmware stored in the memory and having machine-readable instructions that, when executed by the processor, control the processor to: capture, at intervals, raw sensor data from the at least one polymer sensor; processing, using a smoothing algorithm, the raw sensor data to generate smoothed sensor data; calculating, for the at least one polymer sensor, a difference between the smoothed sensor data and a baseline; driving, for the at least one polymer sensor, a state machine to change state between a clean air state, an anomalous behavior state, and an anomaly detected state, based upon the difference; and sending, via the wireless interface, an anomaly detected report indicating detected smoking to a cloud detection service when the state is the anomaly detected state.

(AM) A service quality control method, including: generating a beacon using a wireless interface of a beacon device positioned within a serviceable space; receiving, from a mobile device in response to the mobile device detecting the wireless beacon, a first message including a mobile device identifier (ID) that uniquely identifies the mobile device and a beacon ID, decoded from the beacon, that uniquely identifies the beacon device; and updating a database to indicate the association of the mobile device ID with the beacon ID to indicate servicing of the serviceable space.

(AN) The service quality control method denoted as (AM) further including sending, to the mobile device, a service requirement for the serviceable space defined within servicing requirements of the database.

(AO) Either of the service quality control methods denoted as (AM) or (AN) further including: determining, from the database, that the serviceable space has not been serviced; and sending a service alert to a client device associated with the space.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method for generating an air quality event alert for a monitored space having a sensing device, comprising:
    receiving, within a cloud detection service and from the sensing device, an anomaly detected report including a timestamp for an air quality anomaly detected at the monitored space;
    retrieving raw sensor data captured by the sensing device using a plurality of sensors during a period including the timestamp, the plurality of sensors including each of a temperature sensor, a humidity sensor, an atmospheric pressure sensor, a volatile organic compound sensor, and a proximity sensor;
    extracting characteristics and metrics from the raw sensor data for each of the plurality of sensors;
    processing the characteristics and metrics through a model prediction service to generate probabilities indicative of the characteristics and metrics corresponding to profiles of air quality events;
    assembling the probabilities to generate a score for the air quality anomaly corresponding to an important air quality event; and sending an air quality report when the score is higher than a first threshold corresponding to significant air quality events.

2. The method of claim 1, further comprising dismissing the air quality anomaly when the score is lower than a second threshold corresponding to insignificant air quality events.

3. The method of claim 2, further comprising marking the air quality anomaly for later analysis when the score is greater than the second threshold and less than a third threshold lower than the first threshold.

4. The method of claim 3, further comprising generating the air quality report for manual review when the score is less than the first threshold and greater than the third threshold.

5. The method of claim 1, further comprising, before said retrieving, storing the raw sensor data in a data buffer for at least forty-five minutes.

6. A method for detecting an air quality anomaly at a monitored space, comprising:
   capturing, at intervals in a sensing device located at the monitored space, raw sensor data from an environmental sensor, a carbon monoxide (CO) sensor, and a polymer sensor, the environmental sensor including a temperature sensor, a humidity sensor, an atmospheric pressure sensor, a volatile organic compound sensor, and a proximity sensor;
   processing, using a smoothing algorithm, the raw sensor data to generate smoothed sensor data;
   calculating, for at least of the CO sensor and the polymer sensor, a difference between the smoothed sensor data and a baseline;
   driving, for at least of the CO sensor and the polymer sensor, a state machine to change state between a clean air state, an anomalous behavior state, and an anomaly detected state, based upon the difference; and
   sending an anomaly detected report, indicating the air quality anomaly, to a cloud detection service when the state is the anomaly detected state.

7. The method of claim 6, the smoothing algorithm comprising an exponential smoothing algorithm.

8. The method of claim 6, the baseline comprising smoothed sensor data calculated five-minutes earlier.

9. The method of claim 6, further comprising storing the raw sensor data in a data buffer for at least forty-five minutes.

10. The method of claim 9, further comprising sending the raw sensor data from the data buffer to the cloud detection service in response to a request for the raw sensor data from the cloud detection service.

11. A system for monitoring air quality of a monitored space, comprising:
   a sensing device, located at the monitored space, comprising:
   an environmental sensor positioned to sense a characteristic of air within the monitored space, the environmental sensor including a temperature sensor, a humidity sensor, an atmospheric pressure sensor, a volatile organic compound sensor, and a proximity sensor;
   a carbon monoxide (CO) sensor positioned to sense a level of CO in the air;
   a polymer sensor positioned to sense a level of a targeted molecule in the air;
   an interface for communicating with a local network;
   a processor communicatively coupled with a memory; and
   detector firmware stored in the memory and having machine-readable instructions that, when executed by the processor, control the processor to:
      capture, at intervals, raw sensor data from the environmental sensor, the CO sensor, and the polymer sensor;
      process, using a smoothing algorithm, the raw sensor data to generate smoothed sensor data;
      calculate, for at least the CO sensor and the polymer sensor, a difference between the smoothed sensor data and a baseline;
      drive, for at least the CO sensor and the polymer sensor, a state machine to change state between a clean air state, an anomalous behavior state, and an anomaly detected state, based upon the difference; and
      send, via the interface, an anomaly detected report, indicating an air quality anomaly, to a cloud detection service when the state is the anomaly detected state; and
   the cloud detection service comprising:
   a collection service for receiving the anomaly detected report and for receiving the raw sensor data from the sensing device;
   a model prediction service for processing characteristics and metrics of the raw sensor data to generate probabilities indicative of the characteristics and metrics corresponding to profiles of air quality events;
   a prediction assembling service for assembling the probabilities to generate a score for the air quality anomaly; and
   an anomaly dispatcher for sending an air quality report when the score is higher than a first threshold, the first threshold defining a value corresponding to a high probability that the raw sensor data indicates a significant air quality event.

12. The system of claim 11, the polymer sensor targeting molecules of one or more of tobacco smoke, marijuana smoke, vaping, toxins, small molecules, bacteria, and viruses.

13. A computer-readable media storing machine-readable instructions that, when executed by a computer, perform steps for detecting an air quality anomaly at a monitored space, comprising:
   instructions for capturing, at intervals, raw sensor data from an environmental sensor, a carbon monoxide (CO) sensor, and a polymer sensor, the environmental sensor including a temperature sensor, a humidity sensor, an atmospheric pressure sensor, a volatile organic compound sensor, and a proximity sensor;
   instructions for processing, using a smoothing algorithm, the raw sensor data to generate smoothed sensor data;
   instructions for calculating, for at least the CO sensor and the polymer sensor, a difference between the smoothed sensor data and a baseline;
   instructions for driving, for at least the CO sensor and the polymer sensor, a state machine to change state between a clean air state, an anomalous behavior state, and an anomaly detected state, based upon the difference; and
   instructions for sending an anomaly detected report, indicating the air quality anomaly, to a cloud detection service when the state is the anomaly detected state.

14. The computer-readable media of claim 13, further comprising instructions for storing the raw sensor data in a data buffer for at least forty-five minutes.

15. The computer-readable media of claim 13, the anomaly detected report including a timestamp that stores when the anomalous behavior state was detected.

\* \* \* \* \*